(12) United States Patent
Aharoni et al.

(10) Patent No.: US 12,232,496 B2
(45) Date of Patent: Feb. 25, 2025

(54) METHODS AND SYSTEM FOR STIMULATING ROOT EXUDATION IN PLANTS

(71) Applicant: YEDA RESEARCH AND DEVELOPMENT CO. LTD, Rehovot (IL)

(72) Inventors: Asaph Aharoni, Tel Aviv (IL); Elisa Korenblum, Rehovot (IL)

(73) Assignee: YEDA RESEARCH AND DEVELOPMENT CO. LTD, Rehovot (IL)

( * ) Notice: Subject to any disclaimer, the term of this patent is extended or adjusted under 35 U.S.C. 154(b) by 1074 days.

(21) Appl. No.: 17/040,227

(22) PCT Filed: Mar. 21, 2019

(86) PCT No.: PCT/IL2019/050322
§ 371 (c)(1),
(2) Date: Sep. 22, 2020

(87) PCT Pub. No.: WO2019/180722
PCT Pub. Date: Sep. 26, 2019

(65) Prior Publication Data
US 2021/0007363 A1 Jan. 14, 2021

(30) Foreign Application Priority Data
Mar. 22, 2018 (IL) .......................................... 258319

(51) Int. Cl.
| | | |
|---|---|---|
| *A01N 63/20* | (2020.01) | |
| *A01G 29/00* | (2006.01) | |
| *A01N 63/38* | (2020.01) | |
| *A61K 36/185* | (2006.01) | |
| *A61K 36/81* | (2006.01) | |
| *C07D 305/14* | (2006.01) | |
| *C07J 17/00* | (2006.01) | |

(52) U.S. Cl.
CPC ............. *A01N 63/20* (2020.01); *A01G 29/00* (2013.01); *A01N 63/38* (2020.01); *A61K 36/185* (2013.01); *A61K 36/81* (2013.01); *C07D 305/14* (2013.01); *C07J 17/005* (2013.01); *A61K 2236/00* (2013.01)

(58) Field of Classification Search
None
See application file for complete search history.

(56) References Cited

U.S. PATENT DOCUMENTS

| 4,953,322 A | 9/1990 | Edwards |
| 7,350,331 B1 | 4/2008 | Gontier et al. |
| 2002/0132021 A1 | 9/2002 | Raskin et al. |

FOREIGN PATENT DOCUMENTS

| WO | 2007088024 A1 | 8/2007 |
| WO | 2015200902 A2 | 12/2015 |

OTHER PUBLICATIONS

Oburger, Eva & Dell-mour, Madeleine & Hann, Stephan & Wieshammer, Gottfried & Puschenreiter, Markus & Wenzel, Walter. (2013). Evaluation of a novel tool for sampling root exudates from soil-grown plants compared to conventional techniques. Environmental and Experimental Botany. 87. 235-247. 10.1016/j.envexpbot.2012.11.007.

Oburger E. and Jones, D. (2018) Sampling root exudates—mission impossible?, Rhizosphere, 6, pp. 116-133, https://doi.org/10.1016/j.rhisph.2018.06.004.

Zhang, G., Raza, W., Wang, X., Ran, W., & Shen, Q. (2012). Systemic modification of cotton root exudates induced by arbuscular mycorrhizal fungi and *Bacillus vallismortis* HJ-5 and their effects on *Verticillium wilt* disease. Applied Soil Ecology, 61, 85-91. doi: 10.1016/j.apsoil.2012.02.003.

Marschner, P., Crowley, D.E. & Higashi, R.M. Root exudation and physiological status of a root-colonizing fluorescent pseudomonad in mycorrhizal and non-mycorrhizal pepper (*Capsicum annuum* L.). Plant and Soil 189, 11-20 (1997). https://doi.org/10.1023/A:1004266907442.

Sykłowska-Baranek, K., Pilarek, M., Bonfill, M. et al. Perfluorodecalin-supported system enhances taxane production in hairy root cultures of *Taxus x media* var. *Hicksii* carrying a taxadiene synthase transgene. Plant Cell Tiss Organ Cult 120, 1051-1059 (2015). https://doi.org/10.1007/s11240-014-0659-1.

Ziegler J, Schmidt S, Chutia R, Müller J, Böttcher C, Strehmel N, Scheel D, Abel S. Non-targeted profiling of semi-polar metabolites in *Arabidopsis* root exudates uncovers a role for coumarin secretion and lignification during the local response to phosphate limitation. J Exp Bot. Mar. 2016;67(5):1421-32. doi: 10.1093/jxb/erv539. Epub Dec. 17, 2015. PMID: 26685189; PMCID: PMC4762384.

Kuijken, René & Snel, Jan & Heddes, Martijn & Bouwmeester, Harro & Marcelis, L.F.M.. (2014). The importance of a sterile rhizosphere when phenotyping for root exudation. Plant and Soil. 387. 131-142. 10.1007/s11104-014-2283-6.

Bais HP, Park SW, Weir TL, Callaway RM, Vivanco JM. How plants communicate using the underground information superhighway. Trends Plant Sci. Jan. 2004;9(1):26-32. doi: 10.1016/j.tplants.2003.11.008. PMID: 14729216.

Poole P, Ramachandran V, Terpolilli J. Rhizobia: from saprophytes to endosymbionts. Nat Rev Microbiol. May 2018; 16(5):291-303. doi: 10.1038/nrmicro.2017.171. Epub Jan. 30, 2018. PMID: 29379215.

(Continued)

*Primary Examiner* — Michael V Meller
(74) *Attorney, Agent, or Firm* — The Roy Gross Law Firm, LLC; Roy Gross

(57) ABSTRACT

Provided is a plant exudate, methods for obtaining a plant exudate by inducing the plant to secrete an exudate and systems for the collection of a plant exudate which include: one or more plant container including at least two discrete compartments each configured to accommodate a split root of a plant, the compartments being a root stimulating compartment including one or more input being in fluid communication with at least a source of a plant root stimulant, and a root exudate harvesting compartment, and a root exudate collection compartment in fluid communication with the root exudate harvesting compartment.

3 Claims, 18 Drawing Sheets

(56) References Cited

OTHER PUBLICATIONS

Wirthmueller L, Maqbool A, Banfield MJ. On the front line: structural insights into plant-pathogen interactions. Nat Rev Microbiol. Nov. 2013;11(11):761-76. doi: 10.1038/nrmicro3118. Epub Oct. 8, 2013. PMID: 24100360.

Chialva M, Salvioli di Fossalunga A, Daghino S, Ghignone S, Bagnaresi P, Chiapello M, Novero M, Spadaro D, Perotto S, Bonfante P. Native soils with their microbiotas elicit a state of alert in tomato plants. New Phytol. Dec. 2018;220(4):1296-1308. doi: 10.1111/nph.15014. Epub Feb. 9, 2018. PMID: 29424928.

Sonawane PD, Pollier J, Panda S, Szymanski J, Massalha H, Yona M, Unger T, Malitsky S, Arendt P, Pauwels L, Almekias-Siegl E, Rogachev I, Meir S, Cárdenas PD, Masri A, Petrikov M, Schaller H, Schaffer AA, Kamble A, Giri AP, Goossens A, Aharoni A. Plant cholesterol biosynthetic pathway overlaps with phytosterol metabolism. Nat Plants. Dec. 22, 2016;3:16205. doi: 10.1038/nplants.2016.205. Erratum in: Nat Plants. Jun. 12, 2017;3:17101. PMID: 28005066.

Djerassi, C. et al. Mass Spectrometry in Structural and Stereochemical Problems, IV. Vindolinine. Proceedings of the National Academy of Sciences of the United States of America. Feb. 1962;48(2):113. https://doi.org/10.1073/pnas.48.2.113.

El-Sayed, M., Verpoorte, R. Catharanthus terpenoid indole alkaloids: biosynthesis and regulation. Phytochem Rev 6, 277-305 (2007). https://doi.org/10.1007/s11101-006-9047-8.

Hirasuna, T.J., Pestchanker, L.J., Srinivasan, V. et al. Taxol production in suspension cultures of *Taxus baccata* . Plant Cell Tiss Organ Cult 44, 95-102 (1996). https://doi.org/10.1007/BF00048185.

Hoffland et al. "Root exudates What are they, what are their functions and how can we collect them" Wageningen University and Research (2016).

Massalha H, Korenblum E, Tholl D, Aharoni A. Small molecules below-ground: the role of specialized metabolites in the rhizosphere. Plant J. May 2017;90(4):788-807. doi: 10.1111/tpj.13543. Epub Apr. 22, 2017. PMID: 28333395.

Van Dam NM, Bouwmeester HJ. Metabolomics in the Rhizosphere: Tapping into Belowground Chemical Communication. Trends Plant Sci. Mar. 2016;21(3):256-265. doi: 10.1016/j.tplants.2016.01.008. Epub Jan. 30, 2016. PMID: 26832948.

Mommer L, Kirkegaard J, van Ruijven J. Root-Root Interactions: Towards a Rhizosphere Framework. Trends Plant Sci. Mar. 2016;21(3):209-217. doi: 10.1016/j.tplants.2016.01.009. Epub Jan. 30, 2016. PMID: 26832947.

Nath, L., Gorantla, J., Thulasidasan, A. et al. Evaluation of uttroside B, a saponin from *Solanum nigrum* Linn, as a promising chemotherapeutic agent against hepatocellular carcinoma. Sci Rep 6, 36318 (2016). https://doi.org/10.1038/srep36318.

Semchenko, M. et al. "Plant root exudates mediate neighbour recognition and trigger complex behavioural changes" New Phytologist. Nov. 1, 2014;204(3):631-7. https://doi.org/10.1111/nph.12930.

PCT International Search Report for International Application No. PCT/IL2019/050322, mailed May 21, 2019, 4pp.

PCT Supplemental International Search Report for International Application No. PCT/IL2019/050322, mailed Apr. 9, 2020, 9pp.

PCT Written Opinion for for International Application No. PCT/IL2019/050322, mailed May 21, 2019, 7pp.

PCT International Preliminary Report on Patentability for International Application No. PCT/IL2019/050322, issued Sep. 22, 2020, 8pp.

Figure 15A
Figure 15B
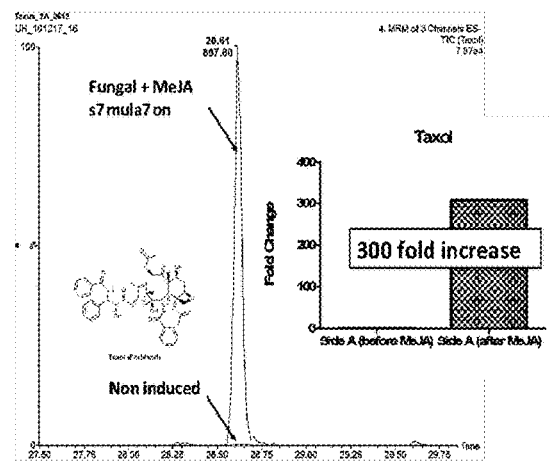
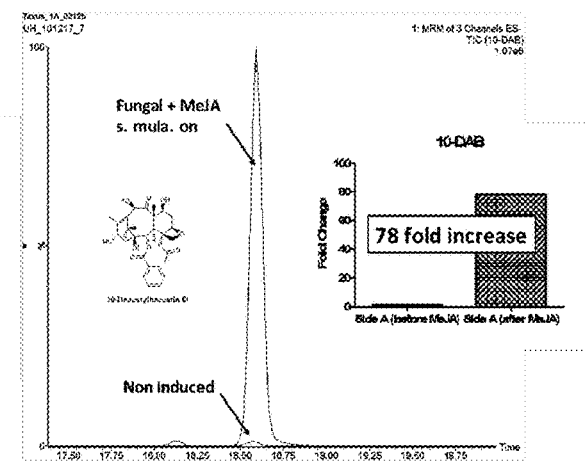
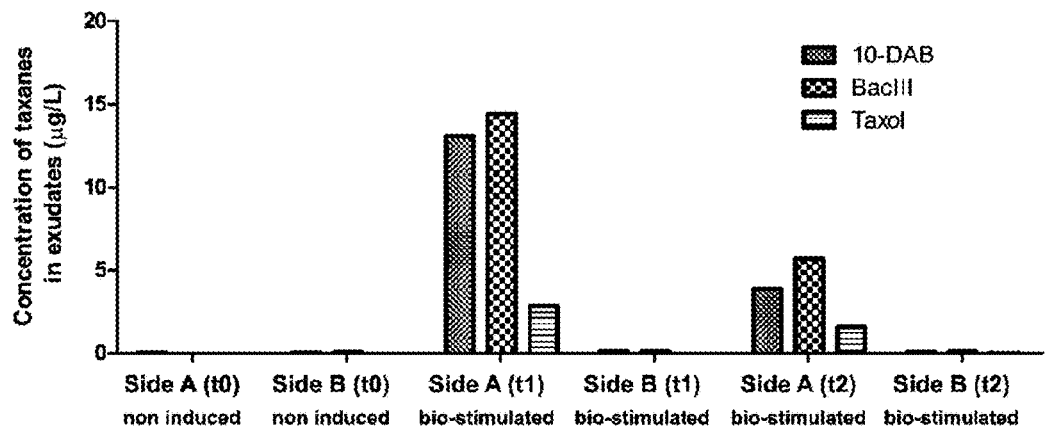
Figure 15c

Figure 16A
Figure 16B
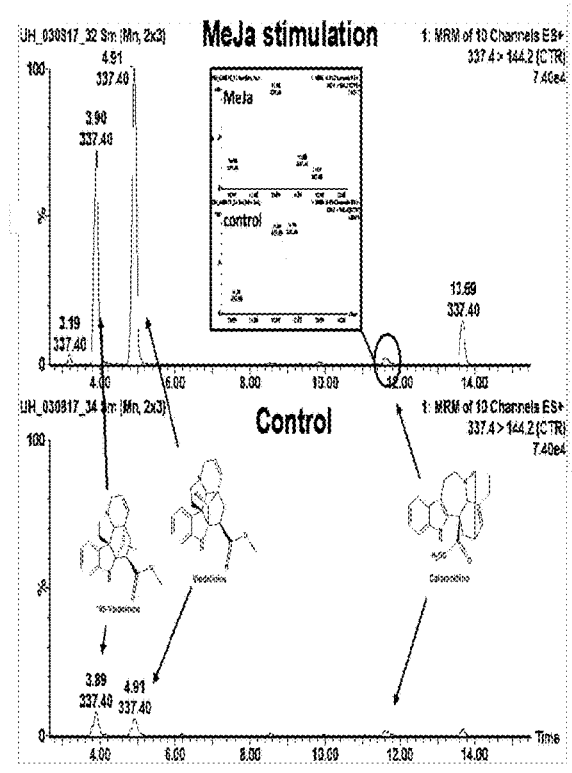
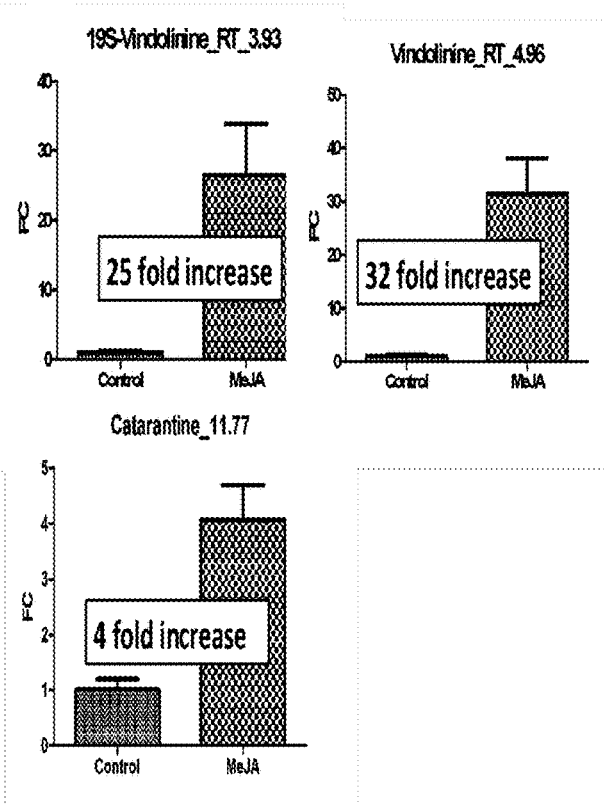

METHODS AND SYSTEM FOR STIMULATING ROOT EXUDATION IN PLANTS

CROSS REFERENCE TO RELATED APPLICATIONS

This application is a National Phase of PCT Patent Application No. PCT/IL2019/050322 having International filing date of Mar. 21, 2019, entitled "METHODS AND SYSTEM FOR STIMULATING ROOT EXUDATION IN PLANTS", which claims the benefit of priority from Israeli patent application No. 258319 filed Mar. 22, 2018, entitled "METHODS FOR STIMULATING METABOLITE PRODUCTION AND EXUDATION IN PLANTS." The contents of the above applications are all incorporated by reference as if fully set forth herein in their entirety.

FIELD OF THE INVENTION

The present invention relates to methods for inducing a plant to exudate a compound or compounds of interest and to new compound/s and combinations thereof.

BACKGROUND OF THE INVENTION

The plant kingdom produces hundreds of thousands of different compounds that are often genus or family specific.

Some molecules are primary metabolites of the plant, while others, referred to as secondary or 'specialized' metabolites, are not vital to cells that produce them, but contribute to the overall fitness of the organisms. Alkaloids are one example of secondary metabolites. They are low molecular weight nitrogen-containing organic compounds, typically with a heterocyclic structure. Alkaloid biosynthesis in plants is tightly controlled during development and in response to stress and pathogens.

The broad group of triterpenoid-alkaloid compounds is widespread in plants and derived from the cytosolic mevalonic acid isoprenoid biosynthetic pathway. Steroidal saponins and steroidal alkaloids are two large classes of triterpenoids produced by plants. Steroidal alkaloids (SAs), also known as "*Solanum* alkaloids" are common constituents of numerous plants belonging to the Solanaceae family, particularly of the genus *Solanum*. SAs are also produced by a large number of species in the Liliaceae family.

Estimated in the order of 1350 species, *Solanum* is one of the largest genera of flowering plants, representing about a half of the species in the Solanaceae. Diverse structural composition and biological activity, as well as occurrence in food plants including tomato (*Solanum lycopersicum*), potato (*Solanum tuberosum*) and eggplant (*Solanum melongena*), made SAs the subject of extensive investigations (Eich E. 2008. Solanaceae and Convolvulaceae—secondary metabolites: biosynthesis, chemotaxonomy, biological and economic significance: a handbook. Berlin: Springer). In addition, tomato roots also secrete strigolactones and other organic acids.

The valuable specialized metabolites of many plants have motivated the market interest on many industrial sectors, such as drug sources, fungicides and insecticides, natural flavoring and coloring substances, as well as natural scents and oils.

For example, *Taxus* species, such as *T. media, T. cuspidate, T. baccata*, and *T. mairei* are important medicinal plants. These plants are the unique source of Taxol (paclitaxel), a diterpenoid with an alkaloidal side chain, one of the most effective anti-cancer drugs available on the market. Taxol stabilizes mitotic microtubule polymerization, consequently affecting cell division. Unfortunately, limited amounts are extracted from the host plants. A complete treatment of a single patient requires approximately eight 60-year-old yew trees. Moreover, *Taxus* plant growth is geographically and seasonally restricted, and there is no reliable alternative. The synthesis of Taxol from geranylgeranyl diphosphate (the diterpenoid precursor) involves at least 20 distinct enzymatic steps, and its complex structure hinders its chemical synthesis economically on an industrial level.

The second most used phytochemicals with high anti-cancer activity are vinca alkaloids obtained from the Madagascar periwinkle plant (*Catharanthus roseus*). This group of anti-cancer compounds blocks cell division by depolymerizing the microtubule. Two natural vinca alkaloids, vinblastine and vincristine, are currently in clinical use. *Catharanthus roseus* also contains an enormous variety (approximately 120) of other terpenoid indole alkaloids. These metabolites are derivative from the central precursor strictosidine, formed by the condensation of tryptamine and secologanin, which are derived from the shikimate pathway and from the plastidic non-mevalonate pathway, respectively. As with Taxol, only low amounts of vinca metabolites can be obtained from either cultivated or wild plants.

*Cannabis sativa* (marijuana) is a source of cannabinoids, including tetrahyrocannabinol (THC) and cannabidiol (CBD). The compounds have been studied for their role in the alleviation of pain and other conditions.

The opium poppy (*Pappaver somniforum*) is used by the pharmaceutical industry not only as a source of opium, but also as a source of other alkaloids, such as thebaine and oripavine, that are processed into drugs, such as codeine and oxycodone. These compounds have also been studied for their role in the alleviation of pain.

Many plant-based products available in the market are extracted from cultivated plants (e.g., with long cultivation periods) or plants in the wild (e.g., which may be geographically restricted). Therefore, there is a great demand for non-destructive alternative ways to obtain these molecules and in continuous production, such as growing plants in self-contained up-scaled non-soil systems (e.g., hydroponics and aeroponics). Plants may translocate 20-50% of total photosynthates to their roots, and up to 70% of the sink root metabolites are exuded into soil. However, breakdown of metabolites often occurs in conventional non-sterile growth systems due to microbial metabolism. Growing plants in sterile systems has been shown to prevent the breakdown of these molecules, and consequently, they accumulate in root exudates (Kuijken, R. C. P., Snel, J. F. H., Heddes, M. M., Bouwmeester, H. J. and Marcelis, L. F. M. (2014) The importance of a sterile rhizosphere when phenotyping for root exudation. Plant Soil, 387, 131-142. Available at: http://link.springer.com/10.1007/s11104-014-2283-6).

On the other hand, microbes from the soil might have an effect on plant metabolism and exudation. As a result, production of high value molecules by induction of plant exudation by stimulation of plant metabolism has not been considered.

A selected fraction of soil microbes establishes interactions with plants, and some may become successful plant pathogens. The reason for this selection is likely due to the constant and diverse secretion of antimicrobial root exudates (Bais, H. P., Park, S. W., Weir, T. L., Callaway, R. M. and Vivanco, J. M. (2004) How plants communicate using the underground information superhighway. Trends Plant Sci., 9, 26-32).

Specific interactions have been observed described between particular plants and specific microbial species. For example, nitrogen-fixing microbial symbionts beneficial symbiotic relationships betweenand legumes and nitrogen-fixing microbial symbionts have been recognized (Poole, P., Ramachandran, V. and Terpolilli, J. (2018) Rhizobia: from saprophytes to endosymbionts), as have negative effects of plant pathogens (Wirthmueller, L., Maqbool, A. and Banfield, M. J. (2013) On the front line: structural insights into plant-pathogen interactions. Nat. Rev. Microbiol., 11, 761-776. Available at: http://www.ncbi.nlm.nih.gov/pubmed/24100360 [Accessed Oct. 17, 2013].). In addition, root microbiome, the microbial community associated to the root may modulate plant responses (Chialva, M., Salvioli, A., Fossalunga, D., et al. (2018) Native soils with their microbiotas elicit a state of alert in tomato plants. New Phytol.). Various complex interactions that impact plant health and development are still not fully understood.

Sterile hydroponic or aeroponic systems, while simple, do not represent root exudation in field conditions, while soil-based methods it is complicated to separate between molecules from plants vs. molecules from other soil organisms/environmental organisms. Moreover, while rhizodeposition is increased by environmental stresses (e.g., phosphate or iron deficiency), microorganisms, and the presence of solid rooting media, most rhizosphere carbon flow research has been undertaken in sterile solution culture, which tends to exclude sloughed-off root cells and tissues and is not a realistic substitute for plants growing in soil.

Approaches to soil-based exudate sampling targeting the entire root system include (i) growing the plants in soil-filled pots followed by careful root washing (soil removal) and hydroponic exudate sampling; (ii) rhizobox growth and hydroponic sample or container; and (iii) methods of using rhizoboxes in combination with root exudate collection (REC). However, none of these methods can differentiate plant molecules from other organisms.

There is a demand for increased production of plant bioactive metabolites, such as drug sources, fungicides and insecticides, natural flavoring and coloring substances, natural scents and oils, food or nutritional supplements, cosmetics, and the like. In addition, there is a constant need to identify novel plant metabolites, e.g., to provide new treatments for diseases or other health problems, alternatives for patients who suffer from side effects or who have resistant diseases, and/or fungicides and insecticides for new or resistant strains, as well as for other applications, e.g., in the food, cosmetic, supplements, and nutrition fields.

Thus, there is a demand for, and it would highly desirable and advantageous to have, methods for exploiting the beneficial potential of the root microbiome to provide sustainable solutions for raising agricultural crop production of specific plant root exudates and to have systems to enable understanding of the interaction of plants with microbial communities, as well as methods for manipulation of microbiome composition to encourage plant-beneficial relationships in order to increase production of specific plant root exudates, in addition to identifying novel beneficial plant metabolites.

SUMMARY OF THE INVENTION

The present invention relates, in some embodiments, to methods for harvesting of specialized metabolites and high value molecules as well as enriched exudates using various stimulators and methods for obtaining novel metabolites from plants. The present invention relates to methods for inducing plants to increase production of specialized metabolites and other molecules using various stimulators and to methods for obtaining novel metabolites and novel exudate composition from induced plants. The present invention also relates to novel specialized metabolites and other molecules produced thereby. The present invention also relates to the recycling of stimulated plants or portions thereof as sources for exudates or specialized metabolites and other molecules.

In one aspect, the present invention provides a method for producing, eliciting, triggering or increasing production and/or harvesting an exudate from a plant root or from a plant split-root. In one embodiment, the method comprising: providing a plant; splitting a root of the plant into at least two root moieties; placing each root moiety of the plant into a separate container or compartment; stimulating a first root moiety of the plant or an aerial portion of the plant to induce exudation or secretion of an exudate by the first root moiety or by the second root moiety of the plant into the container or compartment of the first root moiety or the second root moiety. In one embodiment, the method further comprises harvesting the exudate from the container or compartment. In one embodiment, the method comprising: providing a plant; placing a root of the plant into a container or a compartment; stimulating the root of the plant or an aerial portion of the plant (with a stimulant or an elicitor) to increase, elicit, trigger induce exudation or secretion of an exudate by the root of the plant into the container or the compartment. In one embodiment, the method further comprises harvesting the exudate from the container or compartment.

In one embodiment, wherein the exudate comprises a metabolite of interest, the method further comprises isolating the metabolite of interest from the exudate.

In one embodiment, the method may include utilizing a control plant stimulated with a vehicle without or devoid of a stimulant or an elicitor. In one embodiment, the intact root of the test plant and the intact root of the control plant are each divided into two equal moieties, each of which is placed into a separate container or compartment. In another embodiment, the intact root of the test plant and the intact root of the control plant are each removed and lateral root moieties generated from each truncated root are each placed into a separate container or compartment.

In another embodiment, a container comprises hydroponics and soil (or soil sample). In another embodiment, a container comprises hydroponics and any stimulant or a combination of stimulants as described herein.

In one embodiment, the method may include utilizing a control plant stimulated with a vehicle without or devoid of a stimulant or an elicitor. In another aspect, the present invention provides a method for obtaining and identifying a previously unidentified plant exudate from a plant root of a plant, the method comprising: providing a test plant; splitting a root of the test plant into at least two root moieties; placing each root moiety of the test plant into a separate container or compartment; providing a control plant; splitting a root of the control plant into at least two root moieties; placing each root moiety of the control plant into a separate container or compartment; stimulating a first root moiety of the test plant or an aerial portion of the test plant to induce exudation or secretion of a plant exudate by the first root moiety or the second root moiety of the test plant into the corresponding container or compartment; collecting the exudate of the test plant from the corresponding container or compartment; collecting the exudate of the analogous root moiety of the control plant; qualitatively and quantitatively analyzing the exudate of the test plant and the exudate of the control plant on an analytical platform to generate data; and applying a statistical analysis to the data to determine a difference between the exudate of the test plant and the exudate of the control plant in type or quantity. In one embodiment, wherein at least the exudate of the test plant comprises a metabolite of interest, the method further comprises characterizing the chemical structure of a metabolite exuded or secreted by the test plant that is not exuded or secreted by the control plant or that is exuded or secreted in a statistically lower quantity by the control plant. In one embodiment, the control plant but not the test plant is stimulated with a vehicle devoid of a stimulant.

In yet another aspect, the present invention provides a previously unidentified plant exudate or a previously unidentified plant metabolite or an intermediate thereof from a plant root of a plant obtained by the method for obtaining and identifying a previously unidentified plant metabolite from a plant root of a plant. In one embodiment, the novel plant exudate or the metabolite or intermediate thereof is used in an assay to screen for anti-fungal, bacterial, insecticidal, or herbicidal activity. In another embodiment, the novel plant exudate or the metabolite or intermediate thereof is used for protection of a crop or for treatment of a harvested fruit or vegetable.

In yet another aspect, the present invention provides a method for obtaining an exudate comprising a taxane from a *Taxus* plant root, comprising: providing a *Taxus* plant; contacting or treating the *Taxus* plant's root or an aerial portion of the *Taxus* plant with a stimulant comprising *Trichoderma hamatum* fungus to induce exudation or secretion of the exudate comprising a taxane by the *Taxus* plant's root, thereby obtaining an exudate comprising a taxane from a *Taxus* plant root. In one embodiment, *Taxus* plant root is a non-split *Taxus* plant root. In one embodiment, "induce exudation" includes: increase exudation and/or de-novo induce exudation of a compound. In one embodiment, "induce exudation" is increase the concentration of a compound or a compound of interest in an exudate. In one embodiment, "induce exudation" is increase the amount of a compound or a compound of interest in an exudate.

In yet another aspect, the present invention provides a plant exudate production and collection system including: one or more plant container including at least two discrete compartments each configured to accommodate one or more moiety of a same split root of a plant, the compartments being a root stimulating compartment including one or more input being in fluid communication with at least a source of a plant root stimulant, and a root exudate harvesting compartment, and a root exudate collection compartment in fluid communication with the root exudate harvesting compartment. In one embodiment, the system further comprises a separator in fluid communication with the root exudate collection compartment configured to isolate a compound, a compound of interest, a metabolite of interest or an intermediate thereof from the exudate.

In some embodiments, the root exudate harvesting compartment is in fluid communication with a source of negative pressure. In some embodiments, the system includes an irrigation network and/or a fertilizer network in communication with a source of water and/or fertilizer and the plant container.

In some embodiments, the plant container includes one or more sensor in communication with one or more hardware processor. The sensor can be one or more of a flowmeter, a thermometer, a hygrometer, a soil moisture sensor, a pH-meter, a thermographic camera, a pressure sensor and a detector of a plant exudate, a metabolite of interest and/or an intermediate thereof.

In some embodiments, hardware processor includes a computer program product including a non-transitory computer-readable storage medium having program code embodied therewith, the program code executable by the hardware processor to activate input of stimulant into the root stimulating compartment to stimulate a first root moiety of the plant or an aerial portion of the plant to induce exudation or secretion of an exudate by the same first root moiety or by a second root moiety of the plant accommodated in the root exudate harvesting compartment. In some embodiments, the program code is executable by the hardware processor to automatically activate and adjust one or more of the source of a plant root stimulant, the source of negative pressure, the irrigation network and the fertilizer network based on information received from the one or more sensor. In some embodiments, the program code is executable by the hardware processor to calculate the efficiency of the production of a metabolite of interest or an intermediate thereof, based on information obtained from the one or more sensor, by comparing input into the plant container of at least the stimulant with volume and/or rate of production of the plant root exudate.

In some embodiments, the root exudate harvesting compartment includes a substrate configured to receive a plant root. The substrate can be absorbent or non-absorbent. The separator can include one or more adsorbent surface configured to adsorb the metabolite of interest or an intermediate thereof isolated from the exudate, e.g., the surface can comprise beads.

Other objects, features and advantages of the present invention will become clear from the following description and drawings.

BRIEF DESCRIPTION OF THE DRAWINGS

FIGS. 15A-15C show MRM-LC-MS/MS analysis of *Taxus* exudates. Total ion current chromatograms of Taxol (A) and 10-DAB (B); side plots highlight the fold increase in exudation after bio-stimulation of *Taxus* seedlings with fungus and methyl jasmonate (Meta). Quantification of taxanes (C) was performed using an external standard curve of 10-DAB, Baccatin III, and Taxol.

FIGS. 16A-16B show MRM-LC-MS/MS analysis of *C. roseus* exudates. Total ion current chromatograms of vinca alkaloids present in the exudates of Root B after methyl jasmonate stimulation (A, top) and control plants (A, bottom). Side plots highlight the fold increase of metabolites exudation (B).

DETAILED DESCRIPTION OF THE INVENTION

Figure 1:
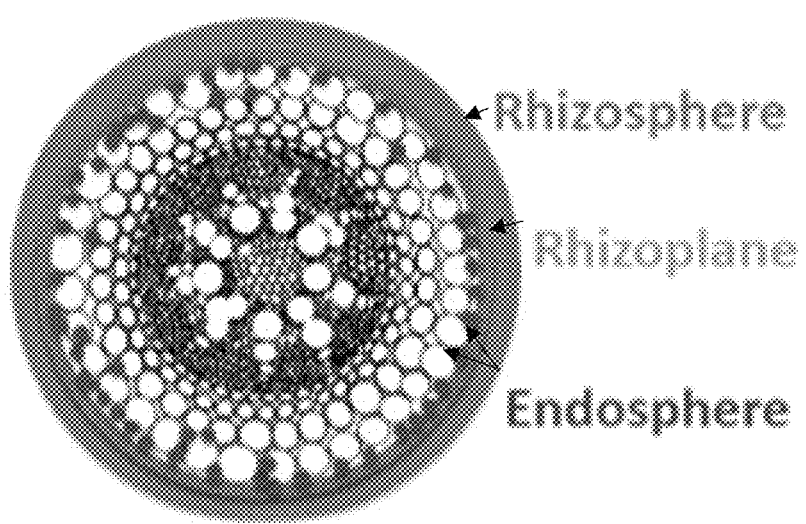
FIG. 1 is a schematic depicting the cross-section of a generic plant root in its surrounding soil. The indicated rhizosphere is the narrow region of surrounding soil directly influenced by root exudates and soil microorganisms. It includes plant cells that have been sloughed off the roots (rhizodeposition). The indicated rhizoplane is the microenvironment of the root system near the surface. The indicated endosphere comprises the endophytes of a plant. Endophytes are endosymbionts (e.g., bacteria or fungi) that live within a plant without causing apparent harm to the plant.

The present invention relates to methods for inducing, triggering and/or eliciting a plant to produce or increase production of an exudate, or of a compound such as a compound of interest and/or a metabolite and/or any other molecule using a stimulator and to methods for obtaining a compound or a compound of interest and/or novel metabolite from induced plants. The present invention also relates to the metabolite and/or a molecule such as described herein. In one embodiment, the present invention provides a method for obtaining an exudate from a plant root of a plant, comprising: providing a plant; splitting a root of the plant into at least two root moieties: a first root moiety and a second root moiety; placing each of the first root moiety and the second root moiety in a separate container or compartment; stimulating or contacting a first root moiety of the plant or an aerial portion of the plant with a stimulant to induce exudation or secretion of an exudate by the first root moiety or by the second root moiety of the plant into the container or compartment of the first root moiety or the second root moiety. In one embodiment, the method further comprises harvesting the exudate from the container or compartment.

In one embodiment, the method comprising: providing a plant; placing a root of the plant into a container or a compartment; stimulating the root of the plant or an aerial portion of the plant (with a stimulant or an elicitor) to increase, elicit, trigger induce exudation or secretion of an exudate by the root of the plant into the container or the compartment. In one embodiment, the method further comprises harvesting the exudate from the container or compartment.

In one embodiment, obtaining comprises increasing production, harvesting or both. In one embodiment, obtaining comprises increasing production or concentration of a molecule of interest with the exudate.

In one embodiment, an exudate or "obtaining an exudate" from a plant root is obtaining a composition comprising at least 10%, 20%, 30%, 40%, 50%, 60%, 70%, 80%, 90%, or 95% w/w (of total composition) exudate. In one embodiment, an exudate or "obtaining an exudate" from a plant root is obtaining a composition comprising at least 10%, 20%, 30%, 40%, 50%, 60%, 70%, 80%, 90%, or 95% w/w (of total composition) exudate without any purification, filtering, concentration, enrichment, and/or cleaning step. In one embodiment, an exudate according to the methods and systems of the invention is an exudate obtained directly from a plant root and/or a first root moiety. In one embodiment, an exudate according to the methods and systems of the invention is an untreated composition comprising at least 10%, 20%, 30%, 40%, 50%, 60%, 70%, 80%, 90%, or 95% w/w (of total composition) exudate. In one embodiment, an untreated composition is a composition that was not cleaned, concentrated, filtered, purified, enriched or any combination thereof.

In one embodiment, a composition comprising at least 10%, 20%, 30%, 40%, 50%, 60%, 70%, 80%, 90%, or 95% w/w (of total composition) exudate is a liquid composition. In one embodiment, a composition comprising at least 10%, 20%, 30%, 40%, 50%, 60%, 70%, 80%, 90%, or 95% w/w (of total composition) exudate, has less than 50%, 40%, 30%, 20%, 10%, 5%, 2%, 1%, 0.5% w/w (of total composition) soil and/or plant growth medium. In one embodiment, a composition comprising at least 10%, 20%, 30%, 40%, 50%, 60%, 70%, 80%, 90%, or 95% w/w (of total composition) exudate, has less than 50%, 40%, 30%, 20%, 10%, 5%, 2%, 1%, 0.5% w/w (of total composition) a soil mineral and/or environmental organism/soil organism/microorganism. In one embodiment, soil mineral is any mineral present in any soil. In one embodiment, environmental organism/soil organism/microorganism is any organism/microorganism present in any soil. In one embodiment, a composition comprising at least 10%, 20%, 30%, 40%, 50%, 60%, 70%, 80%, 90%, or 95% w/w (of total composition) exudate, is devoid of soil and/or plant growth medium. In one embodiment, a composition comprising at least 10%, 20%, 30%, 40%, 50%, 60%, 70%, 80%, 90%, or 95% w/w (of total composition) exudate, is devoid of an environmental organism, a soil organism and/or microorganism.

In one embodiment, the method may include utilizing a control plant stimulated with a vehicle without or devoid of a stimulant or an elicitor. In one embodiment, a "plant stimulated" comprises stimulated: split root of a test plant, a root of a test plant and/or an aerial portion of the test plant.

In one embodiment, an exudate is an exudate comprising Taxol. In one embodiment, a compound of interest comprises Taxol. In one embodiment, a stimulant comprises *Trichoderma hamatum* fungus. In one embodiment, taxane comprises Taxol, 10-DAB, Baccatin III or a combination thereof. In one embodiment, a plant or a test plant as described herein is a *Taxus* plant such as but not limited to *Taxus baccata*.

In one embodiment, a stimulant comprises a microbiome (also referred to as microbiota). In one embodiment, the microbial composition is the total number of bacterial cells, fungal cells, or a combination thereof. In one embodiment, the microbial composition consists bacterial cells and fungal cells. In one embodiment, the microbial composition consists bacterial cells and bacterial medium. In one embodiment, the microbial composition consists bacterial cells and soil. In one embodiment, the microbial composition consists fungal cells and soil.

In one embodiment, the microbial composition of a microbiome or a microbiota has 30-90% Proteobacteria. In one embodiment, the microbial composition of a microbiome or a microbiota has 50-98% Proteobacteria. In one embodiment, the microbial composition of a microbiome or a microbiota has 68-73% Proteobacteria. In one embodiment, the microbial composition of a microbiome or a microbiota has 65-71% Proteobacteria. In one embodiment, the microbial composition of a microbiome or a microbiota has 75-83% Proteobacteria.

In one embodiment, the microbial composition of a microbiome or a microbiota has 8-45% Firmicutes bacteria. In one embodiment, the microbial composition of a microbiome or a microbiota has 12-35% Firmicutes bacteria. In one embodiment, the microbial composition of a microbiome or a microbiota has 26-32% Firmicutes bacteria. In one embodiment, the microbial composition of a microbiome or a microbiota has 16-23% Firmicutes bacteria.

In one embodiment, the microbial composition of a microbiome or a microbiota has 0.2-15% Bacteroidetes. In one embodiment, the microbial composition of a microbiome or a microbiota has 1-8% Bacteroidetes. In one embodiment, the microbial composition of a microbiome or a microbiota has 1-4% Bacteroidetes. In one embodiment, the microbial composition of a microbiome or a microbiota has 3-15% Bacteroidetes. In one embodiment, the microbial composition of a microbiome or a microbiota has 2-9% Bacteroidetes.

In one embodiment, the microbial composition of a microbiome or a microbiota has 0.1-8% Actinobacteria. In one embodiment, the microbial composition of a microbiome or a microbiota has 0.2-5% Actinobacteria. In one embodiment, the microbial composition of a microbiome or a microbiota has 0.5-3% Actinobacteria.

In one embodiment, the microbial composition of a microbiome or a microbiota has less than 4% or even less than 0.5% Cyanobacteria and/or Gemmatimonadetes bacteria. In one embodiment, the microbial composition of a microbiome or a microbiota has less than 2% or even less than 0.5% Cyanobacteria and/or Gemmatimonadetes bacteria. In one embodiment, the microbial composition of a microbiome or a microbiota is devoid of Cyanobacteria and/or Gemmatimonadetes bacteria.

In one embodiment, provided herein is a method for obtaining an exudate comprising a taxane from a *Taxus* plant root, comprising: providing a *Taxus* plant and contacting its root with a stimulant comprising the fungus *Trichoderma hamatum*, thereby obtaining an exudate comprising a taxane from a *Taxus* plant root.

In one embodiment, provided herein is a method for obtaining an exudate comprising a taxane from a *Taxus* plant root, comprising: providing a *Taxus* plant; contacting the *Taxus* plant's root or an aerial portion of the *Taxus* plant with a stimulant comprising *Trichoderma hamatum* fungus to induce exudation or secretion of the exudate comprising a taxane by the *Taxus* plant's root, thereby obtaining an exudate comprising a taxane from a *Taxus* plant root. In one embodiment, *Taxus* plant root is a non-split *Taxus* plant root.

In one embodiment, obtaining an exudate comprises inducing exudation. In one embodiment, obtaining an exudate comprises increasing the concentration of a compound or a compound of interest in an exudate. In one embodiment, In one embodiment, obtaining an exudate comprises increasing the amount of a compound or a compound of interest in an exudate.

In one embodiment, provided herein is a method for obtaining an exudate comprising a taxane from a *Taxus* plant root without splitting the root. In one embodiment, provided herein is a method for obtaining an exudate comprising a taxane from a whole *Taxus* plant root without splitting the root. In one embodiment, provided herein is a method for obtaining an exudate comprising a taxane from a whole *Taxus* plant root without splitting the root comprising contacting the root with a stimulant (stimulated root) such as the fungus *Trichoderma hamatum* and obtaing an exudate comprising a taxane from the stimulated root. In one embodiment, provided herein is a method for obtaining an exudate comprising a taxane from a *Taxus* plant root, comprising: providing a *Taxus* plant; placing the *Taxus* plant's root in a container or compartment and stimulating the *Taxus* plant's root or an aerial portion of the *Taxus* plant with a stimulant comprising the fungus *Trichoderma hamatum* to induce exudation or secretion of the exudate comprising the taxane by the the *Taxus* plant's root and into the container or compartment; and possibly further harvesting the exudate comprising a taxane from the container or compartment.

In one embodiment, provided herein is a method for obtaining an exudate comprising a taxane from a *Taxus* plant root, comprising: providing a *Taxus* plant; splitting a root of the *Taxus* plant into at least two root moieties; placing each root moiety of the *Taxus* plant into a separate container or compartment; stimulating a first root moiety of the *Taxus* plant or an aerial portion of the *Taxus* plant with a stimulant comprising the fungus *Trichoderma hamatum* to induce exudation or secretion of the exudate comprising the taxane by the first root moiety or by the second root moiety of the *Taxus* plant into the container or compartment of the first root moiety or the second root moiety; and harvesting the exudate comprising a taxane from the container or compartment. In one embodiment, stimulating comprises contacting with a stimulant.

In one embodiment, provided herein is a method for obtaining an exudate comprising an alkaloid from a Solanaceae plant root, comprising: providing a Solanaceae plant and contacting the Solanaceae plant's root with a stimulant comprising a bacterial composition comprising a Proteobacterium, thereby obtaining an exudate comprising an alkaloid from a Solanaceae plant root. In one embodiment, a bacterial composition is a bacterial consortium.

In one embodiment, provided herein is a method for obtaining an exudate comprising an alkaloid from a Solanaceae plant root, comprising: providing a Solanaceae plant; splitting a root of the Solanaceae plant into at least two root moieties; placing each root moiety of the Solanaceae plant into a separate container or compartment; stimulating a first root moiety of the Solanaceae plant or an aerial portion of the Solanaceae plant with a stimulant comprising a bacterial composition comprising a Proteobacterium, to induce exudation or secretion of the exudate comprising an alkaloid by the first root moiety, by the second root moiety or both; into the container or compartment of: the first root moiety, the second root moiety, or both; thereby obtaining an exudate comprising an alkaloid from a Solanaceae plant.

In one embodiment, the bacterial composition comprises an Actinobacterium, a Bacteroidetes bacterium, a Cyanobacterium, a Firmicutes bacterium, a Gemmatimonadetes bacterium, or any combination thereof. In one embodiment, at least 30% of the bacterial cells in the bacterial composition are Proteobacteria. In one embodiment, 15% to 95% of the bacterial cells in the bacterial composition are Proteobacteria. In one embodiment, 20% to 80% of the bacterial cells in the bacterial composition are Proteobacteria. In one embodiment, 40% to 80% of the bacterial cells in the bacterial composition are Proteobacteria.

In one embodiment, at least 5% of the bacterial cells in said bacterial composition are Firmicutes bacteria. In one embodiment, 5% to 50% of the bacterial cells in said bacterial composition are Firmicutes bacteria. In one embodiment, 10% to 50% of the bacterial cells in said bacterial composition are Firmicutes bacteria. In one embodiment, 20% to 40% of the bacterial cells in said bacterial composition are Firmicutes bacteria.

In one embodiment, 0.05% to 20% of the bacterial cells in said bacterial composition are: Actinobacteria, Bacteroidetes bacteria or a combination thereof. In one embodiment, 0.1% to 10% of the bacterial cells in said bacterial composition are: Actinobacteria, Bacteroidetes bacteria or a combination thereof. In one embodiment, 1% to 15% of the bacterial cells in said bacterial composition are: Actinobacteria, Bacteroidetes bacteria or a combination thereof.

In one embodiment, the Solanaceae plant is a tomato plant. In one embodiment, an alkaloid comprises a saponin. In one embodiment, an alkaloid comprises uttroside B. In one embodiment, the stimulant further comprises methyl jasmonate.

In one embodiment, the container or compartment of: the first root moiety, the second root moiety, or both is the respective container or compartment housing or comprising a first root moiety or a second root moiety but not both. In one embodiment, induce exudation or secretion of the exudate is induce exudation or secretion of the exudate by the first root moiety, the second root moiety, or both. In one embodiment, induce exudation or secretion of the exudate is induce exudation or secretion of the exudate by the first root moiety and not by the second root moiety. In one embodiment, induce exudation or secretion of the exudate comprising the taxane is induce exudation or secretion of the exudate comprising the taxane by the first root moiety and not by the second root moiety.

In one embodiment, a composition comprising an exudate is obtained or harvested from only in the container or compartment housing the first root moiety. In one embodiment, a composition comprising an exudate is obtained or harvested from the container or compartment housing the first root moiety and the container or compartment housing the second root moiety.

The present invention relates, in some embodiments, to methods for inducing plants to increase production of exudates or of specialized metabolites and other molecules using various stimulators and to the specialized and/or novel metabolites and other molecules produced thereby.

The present invention, in some embodiments, includes a split-root growing system for continuous withdrawal of plant specialized metabolites from intact and bio-stimulated plants through root exudation. The approach employs split-root plants. The shoot and one root are used as stimulation sites, and the compartment of the same part of the root or another part of the root is reserved for exudate collection continuously or semi-continuously. Thus, bio-stimulation of plants provides the means to (i) efficiently and cost effectively harvest known high value plant products, (ii) efficiently produce and cost effectively harvest valuable bioactive plant exudates, which can be used directly as high-value products or from which bioactive molecules can be isolated, and (iii) efficiently harvest and add unexplored metabolites to the current industrial repertoire of bioactive molecules. The split-root method is adaptable; growing different plant species may originate a broad array of products (i.e., metabolites from wild and cultivated plants, as well as from transgenic plants). Any plant can be used from water plants, creeping plants, climbing plants, shrubs, bushes, and trees in all sizes. Plants include, but are not limited to, herbs, water plants, grasses, shrubs, bushes, climbers, creepers, trees, saprophytes, parasites, mangroves, bulb and rhizome plants, and any other type. The efficiency and specificity of production of specific metabolites is determined by the use of different stimulators (i.e., unique or combined microorganisms or their derivative metabolites or cell fractions).

In one aspect, it is related to a technology for inducing plants to produce higher yields of specialized molecules using various stimulators (e.g., microbes or small molecules). For example, split-root plants, with two root systems, Root A and B, are grown separately under controlled nutrient conditions without soil, using hydroponics and/or aeroponics, sharing the same aerial part. Root A and/or the aerial part of plants are treated with the stimulators independently from Root B. Exudates or specific molecules are induced systemically and released by one or both root moieties. Locally induced exudates or secreted molecules are harvested or collected either from Root A or Root B or from both. In some instances, the exudate or secreted molecule of interest is harvested or collected from the stimulated moiety of the split root, whereas in other instances, the exudate or secreted molecule of interest is harvest or collected from the non-stimulated moiety of the split root. In some instances, the exudate or secreted molecule of interest is harvest or collected from both moieties of the split root.

In one aspect, the present invention includes a split root growing system for nonstop withdrawal of plant specialized exudates or metabolites (or their intermediates) from intact and bio-stimulated plants through root exudation, thereby withdrawing (or 'tapping') specialized exudates or metabolites (or their intermediates) from induced plants. In one embodiment, the intact root of the plant is divided into two equal moieties, each of which is placed into a separate container or compartment. In one embodiment, the intact root of the plant is divided into two non-equal moieties: a first root moiety and a second root moiety, each of which is placed into a separate container or compartment.

In another embodiment, the primary intact root of the plant is removed, and a first lateral root moiety and a second lateral root moiety are generated, and each is placed into a separate container or compartment.

In other embodiments, genetic engineering can be used to modify root architecture and actually create more root surface space by increasing branching or total root biomass, for example. Root architecture can be altered by many means, including, but not limited to, 1) genetic engineering; 2) genome editing; 3) chemical or radiation mutagenesis; 4) identifying natural varients/spontenous mutations; 5) using plant hormones, e.g., auxins to treat the roots or strigolactones; 6) using inhibitors of hormone biosynthesis, transport, or signaling pathways; 7) treating the plant with *Arrabscular mycorriza* fungi; 8) treating the plant with *Agrobacterium rhizogenes* that induce root hair formation; or 9) using plants themselves as biostimulants. Plants themselves, or a series of plants, can be used as biostimulants in the present invention. A plant of the same or of a different species can serve as a biostimulant. Alternatively, a series of split-root plants (either the same or different species) can be used in pair or in a group or series. In one embodiment, a stimulant comprises a biostimulant.

In one embodiment, the harvesting step further comprises collecting the exudate and passing the exudate through a column to concentrate the exudate on the column. In yet another embodiment, the harvesting step further comprises eluting the metabolite or intermediate thereof from the column. In one embodiment, the harvesting step further comprises collecting the exudate and optionally concentrating the exudate (such as removing an aqueous solution). In yet another embodiment, the harvesting step further comprises eluting or concentrating a metabolite of interest or an intermediate thereof.

In one embodiment, the container or compartment comprises a hydroponic composition. In one embodiment, the container or compartment comprises an exudate. In one embodiment, the container or compartment is adapted to: store an exudate, collect an exudate, concentrate an exudate, enrich an exudate, or any combination thereof. In one embodiment, the container or compartment comprises a composition comprising an exudate as described herein. In another embodiment, the container or compartment comprises an aeroponic composition. In one embodiment, the container or the compartment is/are parts of a hydroponics system. In one embodiment, the container or the compartment is/are parts of a aeroponics system. In one embodiment, a container or a compartment is fed with a plant nutrient or plant medium. In various embodiments, the plant medium comprises soil suspension or autoclaved soil suspension. In one embodiment, the plant medium comprises 0.5× Hoagland nutrient solution. In another embodiment, the plant medium comprises 0.1× MS plant medium. In another embodiment, the plant medium comprises water. However, any plant medium known in the art can be used. Optimal plant media for various plants and different aspects of their respective metabolism are known in the art.

In one embodiment, the present invention provides a method for obtaining an exudate enriched with a molecule of interest from a plant root of a plant, comprising: providing a plant; splitting a root of the plant into at least two root moieties: a first root moiety and a second root moiety; placing each of the first root moiety and the second root moiety in a separate container or compartment; stimulating or contacting a first root moiety of the plant or an aerial portion of the plant with a molecule of interest stimulant (MOIS) to induce exudation or secretion of an exudate enriched with a molecule of interest by the first root moiety, by the second root moiety or both. In one embodiment, MOIS is the stimulant. In one embodiment, a stimulant comprises MOIS.

In one embodiment, each of a separate container or compartment comprises a different composition. In one embodiment, a separate container or compartment comprising the first root moiety comprises a composition comprising an exudate as described herein. In one embodiment, a separate container or compartment comprising the first root moiety comprises a composition comprising an exudate as described herein and is devoid of a stimulant. In one embodiment, a separate container or compartment comprising the first root moiety comprises a composition comprising an exudate as described herein and less than 10% by weight of the amount of stimulant present in a container or compartment comprising the second root moiety. In one embodiment, the first and second root moieties are present in separate containers or compartments.

In one embodiment, a separate container or compartment comprising the second root moiety comprises a composition comprising soil or plant growth media. In one embodiment, a separate container or compartment comprising the second root moiety comprises a stimulant. In one embodiment, a separate container or compartment comprising the second root moiety comprises a stimulant in an amount that is at least 2, 4, 6, 10, 15, 20, 40, 50, 70, 90, 100 times the amount of stimulant present in a separate container or compartment comprising the second root moiety.

In one embodiment, the terms "secretion" and "exudation" are used interchangeably. In one embodiment, MOIS is a stimulant capable of stimulating the secretion of a molecule of interest. In one embodiment, MOIS is a stimulant who stimulates (increases and/or induces) the amount of secretion of a molecule of interest. In one embodiment, MOIS is a stimulant who induces an increase in the concentration of a molecule of interest in an exudate.

In one embodiment, the terms "stimulate" or "increase" include an elevated amount or a concentration of a molecule of interest in an exudate derived from a first root moiety contacted with a stimulant or MOIS as described herein. In one embodiment, an elevated amount or an elevated concentration of a molecule of interest is measured against a reference exudate or a control exudate as described herein. In one embodiment, the plant comprising a first root moiety contacted with a stimulant or MOIS as described herein is a "test plant" or an "induced plant".

In one embodiment, control-exudate is obtained by a process comprising obtaining a control plant and splitting control plant's root into at least two root moieties; wherein at least two root moieties or an aerial portion of the test plant are devoid of the stimulant.

In one embodiment, control-exudate is devoid of a compound of interest. In one embodiment, any separate container or compartment housing a root, a root moiety, a first root moiety, a second root moiety or any combination thereof of the control plant is/are devoid of a stimulant and/or MOIS.

In one embodiment, a reference exudate or a control exudate is an exudate derived from a reference plant/control plant. In one embodiment, a reference exudate or a control exudate is an exudate derived from a reference plant/control plant having a split root or a root wherein any root or any root moiety is devoid of or not in contact with a stimulant or MOIS. In one embodiment, a reference exudate or a control exudate is an exudate derived from a reference plant/control plant having a split root wherein both the first and the second root moieties are devoid of or not in contact with a stimulant or MOIS. In one embodiment, a reference exudate or a control exudate is an exudate derived from a reference plant/control plant wherein the plant or any part thereof is devoid of or not in contact with a stimulant or MOIS. In one embodiment, a reference plant/control plant is of the same species as the "test plant" or the "induced plant". In one embodiment, a reference-plant/control-plant and a test plant/induced plant are at the same growth phase and/or stage. In one embodiment, a reference-plant/control-plant and a test-plant/induced-plant are about the same weight, height or both.

In one embodiment, the quantity of the exudate or the concentration/amount of a compound of interest, is at least 5, 10, 15, 20, 30, 40, 50, 60, 70, 80, 90, 100, 200, 250 or 300 times greater than the quantity of the exudate, the concentration/amount of the compound of interest extracted from the exudate of an analogous root moiety of a non-induced plant of the same species. In one embodiment, the quantity of the exudate or the concentration/amount of a compound of interest, is at least 5, 10, 15, 20, 30, 40, 50, 60, 70, 80, 90, 100, 200, 250 or 300 times greater than the quantity of the exudate, the concentration/amount of the compound of interest extracted from the exudate of a control exudate. In one embodiment, the phrase "compound of interest" comprises "metabolite of interest". In one embodiment, extracted comprises enriched and/or isolated.

In one embodiment, stimulant comprises methyl jasmonate, soil (or soil sample), a microbe, a fungus, an insect, a nematode, a chemical, a radioactive source, another plant or a portion thereof, a root permeability agent; a detergent, a surfactant, or any combination thereof.

In one embodiment, the term "about" includes +/−1%. In one embodiment, the term "about" includes +/−2%. In one embodiment, the term "about" includes +/−5%. In one embodiment, the term "about" includes +/−10%. In one embodiment, the term "about" includes +/−15%. In one embodiment, the term "about" includes +/−20%.

In one embodiment, the first root moiety exudates and/or secrets a volume of exudate which at least 2 times higher compared to the volume of exudate/secretion of the second root moiety. In one embodiment, the first root moiety exudates and/or secrets a volume of exudate which at least 5 times higher compared to the volume of exudate/secretion of the second root moiety. In one embodiment, the first root moiety exudates and/or secrets a volume of exudate which at least 10 times higher compared to the volume of exudate/secretion of the second root moiety. In one embodiment, the first root moiety exudates and/or secrets a volume of exudate which at least 20 times higher compared to the volume of exudate/secretion of the second root moiety. In one embodiment, the first root moiety exudates and/or secrets a volume of exudate which at least 50 times higher compared to the volume of exudate/secretion of the second root moiety.

In one embodiment, the first root moiety exudates and/or secrets an exudate which is at least 2 times more concentrated with the molecule of interest compared to the concentration of the molecule of interest in the exudate of the second root moiety. In one embodiment, the first root moiety exudates and/or secrets an exudate which is at least 5 times more concentrated with the molecule of interest compared to the concentration of the molecule of interest in the exudate of the second root moiety. In one embodiment, the first root moiety exudates and/or secrets an exudate which is at least 10 times more concentrated with the molecule of interest compared to the concentration of the molecule of interest in the exudate of the second root moiety. In one embodiment, the first root moiety exudates and/or secrets an exudate which is at least 15 times more concentrated with the molecule of interest compared to the concentration of the molecule of interest in the exudate of the second root moiety. In one embodiment, the first root moiety exudates and/or secrets an exudate which is at least 20 times more concentrated with the molecule of interest compared to the concentration of the molecule of interest in the exudate of the second root moiety.

In one embodiment, the first root moiety contacted with a MOIS, exudates and/or secrets an exudate which is at least 2 times more concentrated with the molecule of interest compared to the concentration of the molecule of interest in the exudate of the second root moiety In one embodiment, the test-plant or the first root moiety of the test plant exudates and/or secrets a volume of exudate which at least 2 times higher compared to the total volume of exudate/secretion of the control-plant. In one embodiment, the test-plant or the first root moiety of the test plant exudates and/or secrets a volume of exudate which at least 5 times higher compared to the total volume of exudate/ secretion of the control-plant. In one embodiment, the test-plant or the first root moiety of the test plant exudates and/or secrets a volume of exudate which at least 10 times higher compared to the total volume of exudate/secretion of the control-plant. In one embodiment, the test-plant or the first root moiety of the test plant exudates and/or secrets a volume of exudate which at least 15 times higher compared to the total volume of exudate/secretion of the control-plant. In one embodiment, the test-plant or the first root moiety of the test plant exudates and/or secrets a volume of exudate which at least 20 times higher compared to the total volume of exudate/secretion of the control-plant. In one embodiment, the test-plant or the first root moiety of the test plant exudates and/or secrets a volume of exudate which at least 30 times higher compared to the total volume of exudate/ secretion of the control-plant. In one embodiment, the test-plant or the first root moiety of the test plant exudates and/or secrets a volume of exudate which at least 40 times higher compared to the total volume of exudate/secretion of the control-plant. In one embodiment, the test-plant or the first root moiety of the test plant exudates and/or secrets a volume of exudate which at least 50 times higher compared to the total volume of exudate/secretion of the control-plant. In one embodiment, the test-plant or the first root moiety of the test plant exudates and/or secrets a volume of exudate which at least 75 times higher compared to the total volume of exudate/secretion of the control-plant. In one embodiment, the test-plant or the first root moiety of the test plant exudates and/or secrets a volume of exudate which at least 80 times higher compared to the total volume of exudate/ secretion of the control-plant.

In one embodiment, exudate is the only exudate secreted from the first root moiety. In one embodiment, exudate is the total exudate secreted from all root moieties. In one embodiment, exudate is a first exudate, a second exudate or both. In one embodiment, a first exudate is a composition that is secreted by a root or a split root only in the presence of a stimulant. In one embodiment, a second exudate is a composition that is secreted by a root or a split root only without the presence of a stimulant. In one embodiment, a second exudate is a composition that is secreted by a control plant. In one embodiment, a first exudate is a composition that is secreted by a test plant.

In one embodiment, the test-plant exudates and/or secrets an exudate which is at least 2 times more concentrated with the molecule of interest compared to the concentration of the molecule of interest in the exudate of the control-plant. In one embodiment, the test-plant exudates and/or secrets an exudate which is at least 5 times more concentrated with the molecule of interest compared to the concentration of the molecule of interest in the exudate of the control-plant. In one embodiment, the test-plant exudates and/or secrets an exudate which is at least 10 times more concentrated with the molecule of interest compared to the concentration of the molecule of interest in the exudate of the control-plant. In one embodiment, the test-plant exudates and/or secrets an exudate which is at least 15 times more concentrated with the molecule of interest compared to the concentration of the molecule of interest in the exudate of the control-plant. In one embodiment, the test-plant exudates and/or secrets an exudate which is at least 20 times more concentrated with the molecule of interest compared to the concentration of the molecule of interest in the exudate of the control-plant. In one embodiment, the test-plant exudates and/or secrets an exudate which is at least 30 times more concentrated with the molecule of interest compared to the concentration of the molecule of interest in the exudate of the control-plant. In one embodiment, the test-plant exudates and/or secrets an exudate which is at least 50 times more concentrated with the molecule of interest compared to the concentration of the molecule of interest in the exudate of the control-plant. In one embodiment, the test-plant exudates and/or secrets an exudate which is at least 75 times more concentrated with the molecule of interest compared to the concentration of the molecule of interest in the exudate of the control-plant. In one embodiment, the test-plant exudates and/or secrets an exudate which is at least 80 times more concentrated with the molecule of interest compared to the concentration of the molecule of interest in the exudate of the control-plant. In one embodiment, the test-plant exudates and/or secrets an exudate which is at least 100 times more concentrated with the molecule of interest compared to the concentration of the molecule of interest in the exudate of the control-plant. In one embodiment, the test-plant exudates and/or secrets an exudate which is at least 150 times more concentrated with the molecule of interest compared to the concentration of the molecule of interest in the exudate of the control-plant. In one embodiment, the test-plant exudates and/or secrets an exudate which is at least 200 times more concentrated with the molecule of interest compared to the concentration of the molecule of interest in the exudate of the control-plant. In one embodiment, the test-plant exudates and/or secrets an exudate which is at least 250 times more concentrated with the molecule of interest compared to the concentration of the molecule of interest in the exudate of the control-plant. In one embodiment, the test-plant exudates and/or secrets an exudate which is at least 300 times more concentrated with the molecule of interest compared to the concentration of the molecule of interest in the exudate of the control-plant.

The principle aim of metabolomics is to analyze as many compounds as possible in a single run. However, the analytical platform chosen greatly determines the classes of compound that can be detected. When studying rhizosphere interactions mediated by volatiles, gas chromatography-mass spectrometry (GC-MS) is the platform of choice. By contrast, water-soluble secondary metabolites in exudates, such as phenolics or flavonoids, need to be analyzed via liquid chromatography (LC)/liquid chromatography-mass spectrometry (LC-MS).

If there is no prior knowledge of the type of molecules present or when comprehensively profiling an exudate, a combination of platforms may be used. Initially, untargeted analyses merely yield "fingerprints" providing information about difference in composition between or among samples. Visualization techniques, such as heat maps and clustering can be used to highlight the differences.

In one embodiment, the analytical platform is selected from the group consisting of: gas chromatography-mass spectrometry (GC-MS), liquid chromatography (LC), liquid chromatography-mass spectrometry (LC-MS), MRM-LC-MS/MS, heat mapping, and clustering. After applying statistical analysis, including multivariate analysis, such as principal component analysis (PCA) and/or as partial least squares-discriminant analysis (PLS-DA), compounds or features that demonstrate a difference between or among samples can be pinpointed.

In one embodiment, the statistical analysis comprises a multivariate analysis. In one embodiment, the multivariate analysis comprises principal component analysis (PCA) or partial least square-discriminant analysis (PLS-DA).

In one embodiment, the compound of interest is not being produced by the test plant in its natural environment. In one embodiment, the amount of compound of interest produced by the test plant in its natural environment is at least 20% lower than the amount of compound of interest produced in a test plant according to the current methods. In one embodiment, the amount of compound of interest produced by the test plant in its natural environment is at least 50% lower than the amount of compound of interest produced in a test plant according to the current methods. In one embodiment, the amount of compound of interest produced by the test plant in its natural environment is at least 70% lower than the amount of compound of interest produced in a test plant according to the current methods. In one embodiment, the amount of compound of interest produced by the test plant in its natural environment is at least 90% lower than the amount of compound of interest produced in a test plant according to the current methods. In one embodiment, the amount of compound of interest produced by the test plant in its natural environment is at least 95% lower than the amount of compound of interest produced in a test plant according to the current methods. In one embodiment, the amount of compound of interest produced by the test plant in its natural environment is at least 99% lower than the amount of compound of interest produced in a test plant according to the current methods.

In one embodiment, stimulant comprises MOIS. In one embodiment, the amount of compound of interest produced by the test plant devoid of a stimulant is at least 20% lower than the amount of compound of interest produced in a test plant when the first root moiety is contacted with the stimulant. In one embodiment, a test plant devoid of a stimulant is a test plant not in contact or not contacting a stimulant.

In one embodiment, a control plant not stimulated or devoid of a stimulant is of the same species of the test plant wherein its root is not in contact or not contacting a stimulant. In one embodiment, a control plant devoid of a stimulant is of the same species of the test plant wherein its first root moiety is not in the vicinity (at least 20 cm) from a stimulant. In one embodiment, a test plant devoid of a stimulant is a control plant as described herein. In one embodiment, the only difference between a test plant and a control plant is the existence of a stimulant contacting the test plant but not the control plant. In one embodiment, the only difference between a test plant and a control plant is the existence of a stimulant contacting the test plant's root moiety but not the control plant's root moiety.

In one embodiment, the compound of interest comprises a metabolite. In one embodiment, the metabolite is a primary metabolite. In another embodiment, the metabolite is a secondary metabolite.

In one embodiment, the test plant and the control plant are wild plants. In one embodiment, the test plant and the control plant are of the same species. In one embodiment, the test plant and the control plant are seedling plants. In another embodiment, the test plant and the control plant are cultivated plants. In yet another embodiment, the test plant and the control plant are transgenic plants. Transgenic plants include, but are not limited to, plants engineered by genome editing. In one embodiment, the genome editing comprises introducing an activation or repression element. In another embodiment, the transgenic plant overexpresses a coupled transporter protein specific for transporting a molecule of interest or for transporting a range of molecules of interest. In still another embodiment, the transgenic plant exudes an exudate or molecule of interest that is not native to a wild-type plant of the same species or that is not naturally exuded or produced by a wild-type plant of the same species. In yet another embodiment, the transgenic plant further produces a coupled transporter protein specific for transporting the molecule of interest.

In one embodiment, the plant is selected from the group of plants consisting of water plants, creeping plants, climbing plants, shrubs, bushes, and trees. Plants include, but are not limited to, any plant species, including herbs, water plants, grasses, shrubs, bushes, climbers, creepers, trees, saprophytes, parasites, mangroves, bulb and rhizome plants and any other type.

In one embodiment, the plant is a member of the Solanaceae family. In another embodiment, the plant is a member of the *Solanum* genus.

In one embodiment, the plant is a member of the Taxaceae family. In another embodiment, the plant is a member of the *Taxus* genus. In yet another embodiment, the plant is selected from the group consisting of *Taxus media*, *Taxus cuspidata*, *Taxus baccata*, and *Taxus mairei*. In still another embodiment, the plant is *Taxus baccata*.

In one embodiment, the plant is a member of the Apocynaceae family. In another embodiment, the plant is a member of the *Catharanthus* genus. In yet another embodiment, the plant is *Catharanthus roseus*.

In one embodiment, the plant is a member of the Cannabaceae family. In another embodiment, the plant is a member of the *Cannabis* genus. In yet another embodiment, the plant is *Cannabis sativa*.

In one embodiment, the plant is a member of the Pappavaraceae family. In another embodiment, the plant is a member of the *Pappaver* genus. In yet another embodiment, the plant is *Pappaver somniforum* (opium poppy).

In one embodiment, the stimulating step comprises exposure to soil (or soil sample), a soil microbe, a fungus, or a chemical. In one embodiment, the stimulating step comprises exposure to the fungus *Trichoderm hamatum*. In another embodiment, the stimulating step comprises exposure to methyl jasmonate. In yet another embodiment, the stimulating step comprises exposure to one or more volatiles or other airborne compounds. In one embodiment, the method further comprises adding a root permeability agent to increase the quantity of exudate. In one embodiment, the root permeability agent comprises a detergent.

In one embodiment, the stimulating step is followed by an incubating step. In another embodiment, the stimulating step and the incubating step are repeated. In one embodiment, the incubating step comprises a duration of multiple days under normal growth conditions for the species of plant. In one embodiment, the incubating step is for about one week at about 24° C. with a photoperiod of about 16 h. In one embodiment, the stimulating step, the harvesting step, or both are continuous or largely continuous. In another embodiment, the harvesting step is underground.

The present invention further relates to methods for inducing plants to increase production of exudates or of specific specialized metabolites, their intermediates, and other molecules using various stimulators. Examples include, but are not limited to, uttroside B, taxane or a taxane intermediate (e.g., taxol (paclitaxel), 10-deacetylbaccatin III (10-DAB), or baccatin III), or an alkaloid, such as a vinca alkaloid (e.g., vinblastine or vincristine) or a terpenoid indole alkaloid (e.g., vindolinine, 19S-vindolinine, or catarantine). Examples of other pharmaceutical compounds include cannabinoids, as well as opium, thebaine, oripavine, and other alkaloids.

In one embodiment, the intact root of the plant is divided into two equal moieties, each of which is placed into a separate container or compartment. In another embodiment, the primary intact root of the plant is removed, and lateral root moieties are generated from the truncated root are each placed into a separate container or compartment. In one embodiment, the container or compartment is a hydroponics container or compartment. In another embodiment, the container or compartment is an aeroponics container or compartment.

In one embodiment, each container or compartment is fed with plant medium. In various embodiments, the plant medium comprises soil suspension or autoclaved soil suspension. In one embodiment, the plant medium comprises 0.5× Hoagland nutrient solution. In another embodiment, the plant medium comprises 0.1× MS plant medium. In another embodiment, the plant medium comprises water. However, any plant medium known in the art can be used. Optimal plant media for various plants and different aspects of their respective metabolism are known in the art.

In one embodiment, the metabolite is a primary metabolite or a lipid. In another embodiment, the metabolite is a secondary metabolite. In one embodiment, the plant is a wild plant. In another embodiment, the plant is a cultivated plant. In yet another embodiment, the plant is a transgenic plant, or a plant produced by genome editing. In one embodiment, the genome editing comprising introducing an activation or repression element. In another embodiment, the transgenic plant overexpresses a coupled transporter protein specific for transporting a molecule of interest or for transporting a range of molecules of interest inside the root and/or from the root to the environment (liquid medium or soil or any other extracellular matrix). In still another embodiment, the transgenic plant exudes an exudate or molecule of interest that is not native to a wild-type plant of the same species or that is not naturally exuded or produced by a wild-type plant of the same species. In yet another embodiment, the transgenic plant further produces a coupled transporter protein specific for transporting the molecule of interest, e.g., even a single enzyme overexpressed or downregulated in different molecular ways such that the transporter protein is coupled with an engineered pathway in order for the specific transporter protein to transport the molecule of interest out to the environment (e.g., soil, liquid medium, air, etc.).

In one embodiment, the stimulating step comprises exposure to soil (or soil sample), a microbe, a fungus, an insect, a nematode, a chemical, a radioactive source, or another plant or a portion thereof. In one embodiment, the stimulating step comprises exposure to the fungus *Trichoderm hamatum*. In another embodiment, the stimulating step comprises exposure to methyl jasmonate.

In one embodiment, the method further comprises adding a root permeability agent to increase the quantity of exudate. In one embodiment, the root permeability agent comprises a detergent. In one embodiment, the stimulating step is followed by an incubating step. In another embodiment, the stimulating step and the incubating step are repeated. In one embodiment, the incubating step comprises a duration of multiple days under normal growth conditions for the species of plant. In one embodiment, the incubating step is for about one week at about 24° C. with a photoperiod of about 16 h.

An exudate or metabolite (or its intermediate) obtained according to these methods can be screened in an assay for anti-fungal, anti-bacterial, insecticidal, herbicidal, cosmetic, dietary, nutritive, clothing, or medicinal activity. An exudate or metabolite (or its intermediate) having anti-fungal, anti-bacterial or medicinal activity can be formulated for use as a medicament. An exudate or metabolite (or its intermediate) can be formulated for use in a nutritional supplement or a cosmetic. An exudate or metabolite (or its intermediate) having anti-fungal, anti-bacterial, insecticidal, or herbicidal activity can be sprayed on a crop in a greenhouse or in a field or can be used to spray or wash harvested fruits or vegetables or for treatment of packaging for harvested fruits or vegetables. In one embodiment, an exudate is the test plant's exudate.

Stimulated plants or test-plants used to withdraw exudates can be recycled if certain metabolites are accumulated inside the plants, i.e., in roots or aerial parts (shoots, leaves, trunk). Essentially, the bio-stimulated portion of a plant is obtained after the stimulating step, and the metabolite of interest or the intermediate thereof is isolated (e.g., from the root moiety secreting the exudate).

For example, trees, bushes, cacti, and certain other plants are organisms that live for long periods of time, and exudation collection is the primary goal. Nevertheless, when the expected life cycle is about to end, bio-stimulated parts of a longer-lived plant are used directly for 'harvesting' of specialized metabolites and high value molecules, such as by isolated metabolites directly from the bio-stimulated part of the plant (e.g., the root moiety from which the exudate of interest is secreted).

Alternatively, in the case of shoot or root regeneration and re-branching of a tree, bush, cactus, or other longer-lived plant, a bio-stimulated part of the plant is also used for direct 'harvesting' of specialized metabolites and high value molecules. In the case of plants that live for a short-term, methods of recycling bio-stimulated plant parts that also accumulate the candidate metabolite are used. Moreover, some specialized metabolites can be accumulated after bio-stimulation inside the plants only, and the metabolite of interest is harvested directly from the body of the plant.

The present invention also relates to the specialized exudates, metabolites and other molecules produced thereby. In one embodiment, the shoot and one root are used as stimulation sites, and the compartment of the second part of the root is reserved for exudate collection continuously or semi-continuously. Bio-stimulation of plants provides the means to (I) efficiently and cost effectively harvest known high value plant products, and (II) efficiently harvest and add unexplored metabolites to the current industrial repertoire of bioactive molecules, thereby also providing methods for obtaining high value secondary metabolite production. The split root hydroponics is adaptable; growing different plant species may originate a broad array of products (i.e., metabolites) from wild and cultivated plants as well as from transgenic plants. Any plant can be used from water plants, creeping plants, climbing plants, shrubs, bushes and trees in all sizes. The efficiency and specificity of production of specific metabolites is determined by the use of different stimulators (i.e., unique or combined microorganisms or their derivative metabolites or cell fractions).

For example, the source of the bacteria or other microorganisms used for induction of exudation can be from soil but also from any other sources, such as from plants, animals, marine organisms, or the environment (including lakes, oceans, rivers, and other bodies of water).

This approach is flexible and up scalable and has the potential to become a standard industrial production system for high-value products from plants.

A System for Stimulating Metabolite Production and Exudation in Plants

In one aspect, the present invention provides a plant exudate production and collection system 1700 for industrial metabolite production and exudation in plants. Such a system can be housed in a suitably sized indoor facility, e.g., a hangar or greenhouse, or, alternatively and optionally, be housed, at least in part, underground.

Figure 17:
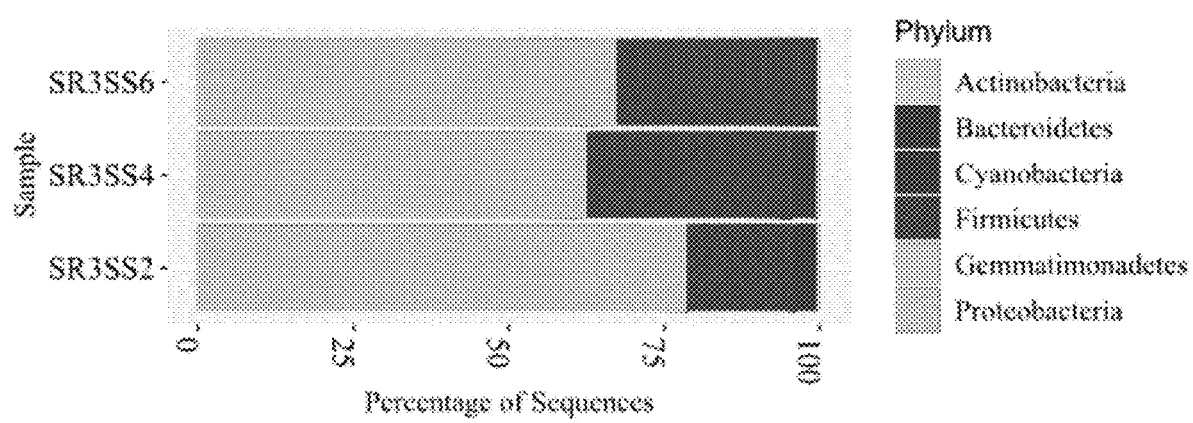
FIG. 17 shows a diagram of the microbial profile or microbiome used to stimulate a Solanaceae plant for the production/exudation of alkaloids. Microbiome SR3 SS6 included about 68-73% Proteobacteria, about 26-32% Firmicutes bacteria, about 1-4% Bacteroidetes, and 0.5-3% Actinobacteria; Microbiome SR3 SS4 included about 66-71% Proteobacteria, about 26-32% Firmicutes bacteria, about 3-14% Bacteroidetes, and 0.5-3% Actinobacteria; Microbiome SR3 SS2 included about 75-83% Proteobacteria, about 16-23% Firmicutes bacteria, about 2-9% Bacteroidetes, and 0.5-3% Actinobacteria. All Microbiome included less than 2% or even less than 0.5% Cyanobacteria and/or Gemmatimonadetes bacteria.
Figure 18:
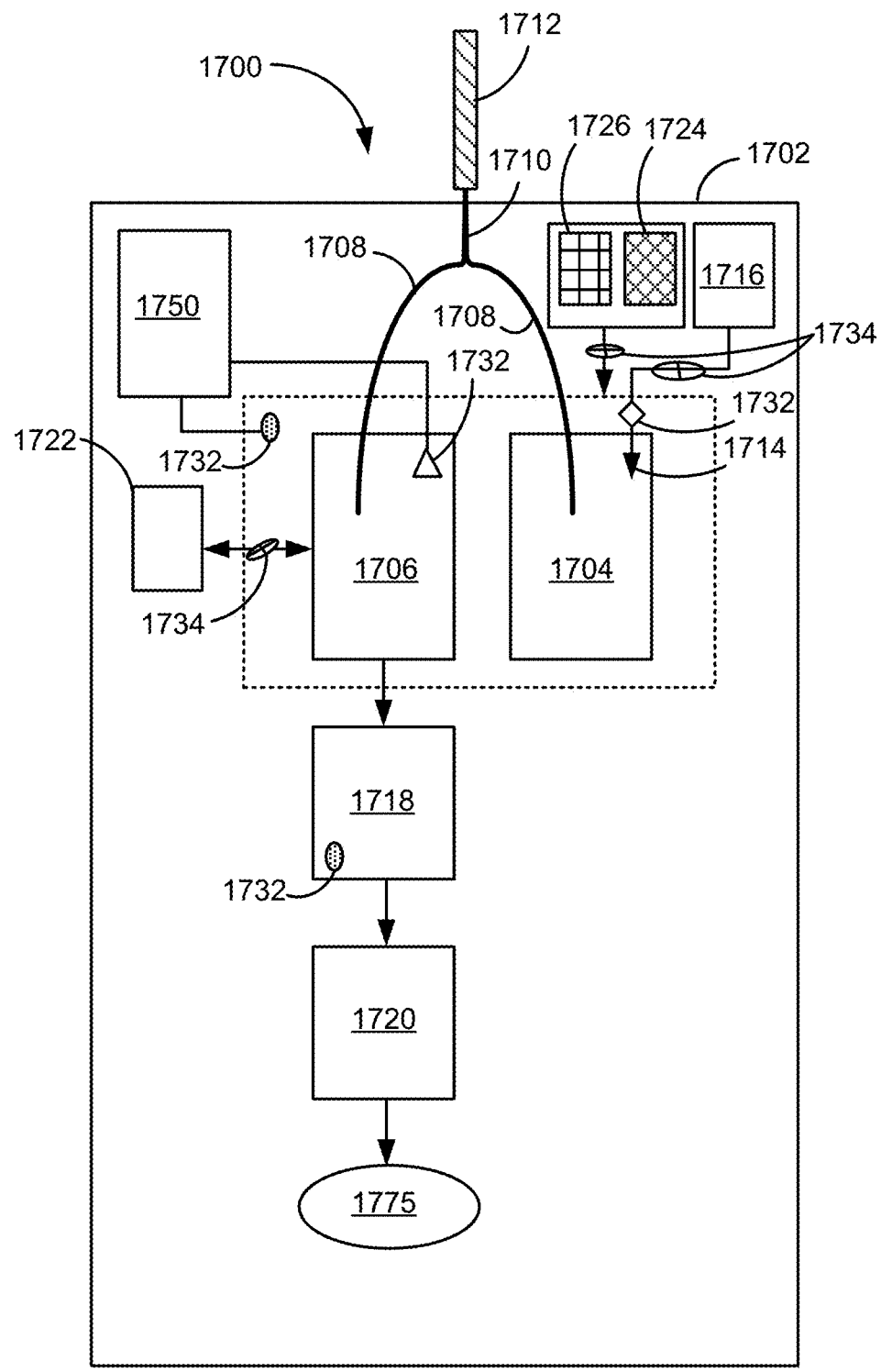
FIG. 18 shows a simplified block diagram of a system for stimulating metabolite production and exudation in plants.

In some embodiments, and as shown in FIG. 17, system 1700 includes one or more plant containers 1702 including at least two discrete compartments 1704/1706, each configured to accommodate one or more moieties 1708 of a same split root 1710 of a plant 1712. As explained in greater detail elsewhere herein, discrete compartments 1704/1706 include a root stimulating compartment 1704 including one or more inputs 1714 being in fluid communication with at least a source of a plant root stimulant 1716, and a root exudate harvesting compartment 1706.

In some embodiments, the system also comprises a root exudate collection compartment 1718 in fluid communication with the root exudate harvesting compartment 1706 and a separator 1720 in fluid communication with the root exudate collection compartment and configured to isolate a metabolite of interest or an intermediate thereof 1775 from the exudate as explained in greater detail elsewhere herein.

In some embodiments, the root exudate harvesting compartment 1706 is in fluid communication with a source of negative pressure 1722. In some embodiments, when activated, the source of negative pressure 1722 creates a mild vacuum in root exudate harvesting compartment 1706 to increase exudate production as well as collection of the exudate, e.g., via a selective membrane, a sieve or other selective media.

In some embodiments, the system includes an irrigation network 1724 and/or a fertilizer network 1726 in communication with a source of water and/or fertilizer and the plant container. This configuration allows for automatic maintenance of the plants.

In some embodiments, the plant container 1702 includes one or more sensors 1732 and valves 1734 in communication with one or more hardware processor 1750. The locations of the sensors 1732 and valves 1734 as depicted in FIG. 17 are exemplary locations and sensors and valves can be located at any suitable location in accordance with their functional designation and in communication with hardware processor 1750. The sensor, for example, can be one or more of a flowmeter, a thermometer, a hygrometer, a soil moisture sensor, a pH-meter, a thermographic camera, a pressure sensor and a detector of a plant exudate, a metabolite of interest and/or an intermediate thereof.

In some embodiments, hardware processor 1750 includes a computer program product including a non-transitory computer-readable storage medium having program code embodied therewith, the program code executable by the hardware processor to activate input of stimulant 1716 into the root stimulating compartment to stimulate a first root moiety of the plant or an aerial portion of the plant to induce exudation or secretion of an exudate by the same first root moiety or by a second root moiety of the plant accommodated in the root exudate harvesting compartment. In some embodiments, the program code is executable by the hardware processor to automatically activate and adjust e.g., via one or more valves 1734, one or more of the sources of a plant root stimulant 1716, the source of negative pressure 1722, the irrigation network 1724 and the fertilizer network 1726 based on information received from the one or more sensors 1732. In some embodiments, the program code is executable by the hardware processor to calculate the efficiency of the production of a metabolite of interest or an intermediate thereof, based on information obtained from the one or more sensor 1732, by comparing input into the plant container 1702 of at least the stimulant 1716 with volume and/or rate of production of the plant root exudate.

In some embodiments, the root exudate harvesting compartment 1706 includes a substrate configured to receive a plant root. The substrate can be absorbent or non-absorbent. The separator can include one or more adsorbent surface configured to adsorb the metabolite of interest or an intermediate thereof isolated from the exudate, e.g., the surface can comprise beads.

DEFINITIONS

As used herein, the singular form "a", "an" and "the" include plural references unless the context clearly dictates otherwise. For example, the term "a molecule" also includes a plurality of molecules.

As used herein, "aeroponics" is the process of growing plants in an air or mist environment without the use of soil or an aggregate medium (known as "geoponics").

As used herein, the "endosphere" comprises all endophytes of a plant.

As used herein, an "extract" is obtained from an "exudate." In a preferred embodiment, the "extract" comprises an active ingredient of interest. The extract may be harvested and used directly without further isolation or purification of the active ingredient. For example, the extract may be used directly in a cosmetic preparation, or as a nutritional, natural health and wellness, medicinal, organic, mineral, food and beverage, dietary, herbal, fitness and body building, bone health, skin care, aging, mental health, healing, male and female sex health, fertility, veterinary (including dog or other pet) health, and human or other animal dietary supplements or for crop protection or fertilization, e.g., for spraying or watering on plant to be protected or fertilized.

As used herein, an "exudate" is a fluid emitted by an organism through pores or a wound. "Exudation" is the process of emitting an "exudate." "Continuous exudation" is exudation which continues regularly and indefinitely during the natural life of the plant.

As used herein, a "stimulant" or "inducer" is a substance that raises levels of physiological activity of the organism.

Preferably, treatment of a plant with a "stimulant" or "inducer" of the present invention directly or indirectly increases levels of exudate or of a component of the exudate (e.g., compound of interest, a primary or secondary metabolite). As used herein, a "stimulant" or "inducer" comprises a composition comprising an inducing molecule, a detergent and/or a surfactant.

As used herein, "harvesting" is the process of collecting and isolating the exuded or secreted exudate or metabolite of interest (or intermediate thereof).

As used herein, "hydroponics" is the process of growing plants without soil ("geoponics"), using mineral nutrient solutions in a water solvent.

As used herein, the "integrated stress response" (ISR) is cellular stress response common to all eukaryotes and has an impact on many critical cellular pathways.

As used herein, "integression" or "integression hybridization" is the movement of a gene (i.e., "gene flow") from the gene pool of one species into the gene pool of another species via repeated backcrossing of an interspecific hybrid with one of its parent species, distinct from simple hybridization and resulting in a complex mix of parental genes.

As used herein, the "metabolome" is the complete set of small molecule chemicals found within a "biological sample" (including, but not limited to, a cell, an organelle, an organ, a tissue, a tissue extract, a biofluid, or an organism). The small molecule chemicals of the metabolome may be "endogenous metabolites" or "exogenous chemicals." "Endogenous metabolites" are naturally produced by an organism and include, but are not limited to, amino acids, organic acids, nucleic acids, fatty acids, amines, sugars, vitamins, cofactors, pigments, and antibiotics. "Exogenous chemicals" are not naturally produced by the organism and include, but are not limited to, drugs, environmental contaminants, food additives, toxins, and other xenobiotics. The "endogenous metabolome" is comprised of the endogenous metabolites, while the "exogenous metabolome" is comprised of the "exogenous chemicals." The "endogenous metabolome" is comprised of a "primary metabolome" and a "secondary metabolome," especially with respect to plants, fungi, and prokaryotes. The "primary metabolome" is comprised of "primary metabolites" (i.e., metabolites directly involved in normal growth, development, and reproduction of the organism), while the "secondary metabolome" is comprised of "secondary metabolites (i.e., metabolites not directly involved in the normal growth, development, or reproduction of the organism). Secondary metabolites often have significant ecological functions.

As used herein, a "metabolite" is usually a small molecule having a molecular weight of less than 1500 Da. A "metabolite" can include, but is not limited to, a glycolipid, a polysaccharide, a short peptide, a small oligonucleotide, an organic acid, a taxane, an alkaloid, and strigolactone, while very large macromolecules (e.g., proteins, mRNA, rRNA, and DNA) are not generally not metabolites and are not part of the metabolome. An "intermediate" of a metabolite is a precursor to the metabolite.

As used herein, a "biomolecule" may comprise not only a "metabolite," but any other also a protein, a peptide, an mRNA, an rRNA, another non-coding RNA, a DNA (genomic or non-genomic). A molecule may be volatile or non-volatile. "RNA" and "DNA" are, respectively, "ribonucleic acid" and "deoxyribonucleic acid."

A "volatile" is a substance that easily evaporates at normal temperatures.

As used herein, a "microbiota" is an ecological community of commensal, symbiotic, and pathogenic microorganisms found in and on all multicellular organisms ("hosts"). Alternatively, as used herein, a "microbiota" is microbiome composed of bacterial cells. "Microbiota" or "microbiome" as used herein is a composition comprising bacteria and devoid of any other organism.

As used herein, "operational taxonomic units (OTU) are used as a pragmatic definition to group individuals by similarity, as pragmatic proxies for microbial "species" at different taxonomic levels. Sequences are clustered according to their similarity to one another, and OTUs are defined based on the similarity threshold (usually 97% similarity, in accordance with accepted standards) of the total community present.

As used herein, a "quantitative trait locus" (QTL) is a section of the DNA (the locus) which correlates with variation in a phenotype (the quantitative trait). As used herein, "expression quantitative trait loci" (eQTL) are genomic loci that contribute to variation in expression levels of mRNA.

As used herein, a "rhizozome" ("creeping rootstalk" or "rootstock") is a modified subterranean stem of a plant that sends out shoots and roots from its nodes.

As used herein, the "rhizoplane" is the microenvironment of a root system near the surface.

As used herein, the "rhizosphere" is the narrow region of soil influenced by root secretions and soil microorganisms and containing many bacteria that feed off the "rhizodeposition" (sloughed-off plant cells) and the proteins and sugars released by the root. It is the site of numerous complexes, symbiotic interactions.

As used herein, a plant "root" is an organ which, in most vascular plants, typically lies below the surface of the soil, although some roots can be aerial. Essentially, the "root" is usually a non-leaf, non-nodes bearing part of the plant body.

As used herein, the "SILVA database" is the SILVA ribosomal RNA database.

As used herein, the term "Solanaceous" refers to a plant of the genus *Solanum*.

All samples obtained from an organism, including those subjected to any sort of further processing are considered to be obtained from the organism.

Methods for DNA isolation, sequencing, amplification, and/or cloning are known to a person skilled in the art. Most commonly used method for DNA amplification is PCR (polymerase chain reaction; see, for example, PCR Basics: from background to Bench, Springer Verlag, 2000; Eckert et al., 1991. PCR Methods and Applications 1:17). Additional suitable amplification methods include the ligase chain reaction (LCR), transcription amplification and self-sustained sequence replication, and nucleic acid based sequence amplification (NASBA). Likewise, methods for RNA and protein isolation, characterization, and the like and for protein expression are known to a person skilled in the art.

The content of steroidal alkaloids and/or steroidal saponins is measured as exemplified herein below and as is known to a person skilled in the art.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

The present invention for withdrawing (or 'tapping') specialized metabolites from induced plants is demonstrated by the following examples. Examples of metabolites from induced plants included potent plant-based anticancer drugs: Taxol (Example 8) and other valuable taxanes produced by *Taxus* (yew) species; vinca alkaloids (Example 10) from *Catharanthus roseus*. In both examples, the addition of stimulators to one root induced exudation of specialized metabolites, from non-detectable amounts to significant concentrations of the said molecules. In addition, steroidal glycoalkaloids (Example 6) from tomato were exuded in higher amounts when specific microbial communities were added to one root, and a new metabolite was also discovered.

Examples of other pharmaceutical compounds may include cannabinoids (from *Cannabis sativa* (marijuana)) (Examples 12 and 13) and opium, thebaine, oripavine, and other alkaloids (from *Pappaver somniforum*) (Examples 14 and 15).

Example 1. Methodology for Inducing Plants to Produce High Amounts of Exudates or Metabolites Using Split Roots In the split-root technology of the present invention, two root systems of one plant are physically separated, allowing one root system to be stimulated (Root A) and to systemically induce the secretion of valuable exudates or valuable metabolites or intermediates, either by the stimulated root system (Root A) or by the non-stimulated root system (Root B) or both. In addition, the aerial part of the same plant may be used as stimulating site or alternatively the site of metabolite harvest following induction of the root system.

In this example, the root systems of seedling plants are divided into two equal parts, and each of the two root system parts is then placed in one of two split-root compartments, each containing plant medium or directly in separate hydroponics or aeroponics containers, each fed with plant medium.

Following stimulation, the plants are incubated for the desired period of time. Incubation may last for several days, a week, or longer. Multiple rounds of stimulation and incubation may be performed. The plant media containing exudates from Root A and Root B are collected, filtered, and extracted. The extracts are analyzed, e.g., by LC-MS and/or GC-MS, and the results are compared using statistical analysis, e.g., including multivariate analysis, such as principal component analysis (PCA) and as partial least square-discriminant analysis (PLS-DA), in order to identify the conditions for maximizing the metabolite exudate of interest.

Larger scale production of the desired metabolite is performed. A large number of plants are grown using the split-root technology, e.g., situations in which treatment of Root A is needed to increase yield of Root B. Alternatively, plants with intact roots are grown, with the root or plant subject to the conditions found to maximize the production of the root exudate of interest.

Example 2. Methodology for Inducing Plants to Produce High Amounts of Exudates or Metabolites Using Split Roots Obtained by Regeneration In the split-root technology of the present invention, two root systems of one plant are physically separated, allowing one root system to be stimulated (Root A) and to systemically induce the secretion of valuable metabolites by the second root system (Root B). In addition, the aerial part of the same plant may be used as stimulating site or alternatively the site of metabolite harvest following induction of the root system. Moreover, local induction of secretion is also obtained from Root A.

Split roots are generated by cutting off the primary root. Lateral roots are then regenerated until they are long enough for the lateral roots to be placed directly in separate hydroponics or aeroponics containers. Each container is fed with plant medium.

Following stimulation, the plants are incubated for the desired period of time. Incubation may last for several days, a week, or longer. Multiple rounds of stimulation and incubation may be performed. The plant media containing exudates from Root A and Root B are collected, filtered, and extracted. The extracts are analyzed, e.g., by LC-MS and/or GC-MS, and the results are compared using statistical analysis, e.g., including multivariate analysis, such as principal component analysis (PCA) and as partial least square-discriminant analysis (PLS-DA), in order to identify the conditions for maximizing the metabolite exudate of interest.

Larger scale production of the desired metabolite is performed, and the desired metabolite is harvested in large quantities.

Example 3: Methodology for Inducing Plants to Produce High Amounts of Exudates or Metabolites Using Split Roots Obtained by Alternative Means In the split-root technology of the present invention, two root systems of one plant are physically separated, allowing one root system to be stimulated (Root A) and to systemically induce the secretion of valuable metabolites by the second root system (Root B). In addition, the aerial part of the same plant may be used as stimulating site or alternatively the site of metabolite harvest following induction of the root system. Moreover, local induction of secretion is also obtained from Root A.

Root architecture is modified by one or more of various means in order to create more root surface space by increasing branching or total root biomass, for example. Root architecture is altered by any one or more of the following means: 1) genetic engineering; 2) genome editing; 3) chemical or radiation mutagenesis; 4) identifying natural varients/spontenous mutations; 5) using plant hormones, e.g., auxins to treat the roots or strigolactones; 6) using inhibitors of hormone biosynthesis, transport, or signaling pathways; 7) treating the plant with *Arrabscular mycorriza* fungi; 8) treating the plant with *Agrobacterium rhizogenes* that induce root hair formation; or 9) using plants themselves as biostimulants.

Roots or root systems are separated or "split" and generated or regenerated until they are long enough for the roots or root systems to be placed directly in separate hydroponics or aeroponics containers. Each container is fed with plant medium.

Following stimulation, the plants are incubated for the desired period of time. Incubation may last for several days, a week, or longer. Multiple rounds of stimulation and incubation may be performed. The plant media containing exudates from Root A and Root B are collected, filtered, and extracted. The extracts are analyzed, e.g., by LC-MS and/or GC-MS, and the results are compared using statistical analysis, e.g., including multivariate analysis, such as principal component analysis (PCA) and as partial least square-discriminant analysis (PLS-DA), in order to identify the conditions for maximizing the metabolite exudate of interest.

Larger scale production of the desired metabolite is performed, and the desired metabolite is harvested in large quantities.

Example 4. Drug Discovery Via Split-Root Methodology

Bio-stimulation used for this technology is also a method for drug discovery. The methods of Example 1, Example 2, or Example 3 are used.

Following stimulation, the plants are incubated for the desired period of time. Incubation may last for several days, a week, or longer. Multiple rounds of stimulation and incubation may be performed. The plant media containing exudates from Root A and Root B are collected, filtered, and extracted. The extracts are analyzed, e.g., by LC-MS and/or GC-MS, and the results are compared using statistical analysis, e.g., including multivariate analysis, such as principal component analysis (PCA) and as partial least square-discriminant analysis (PLS-DA), in order to identify the conditions for maximizing the metabolite exudate of interest.

Induced unidentified metabolites are isolated and characterized and may be tested for safety and/or pharmaceutical efficacy.

Larger scale production of the desired metabolite is performed, and the desired metabolite is harvested in large quantities.

Figure 2A:
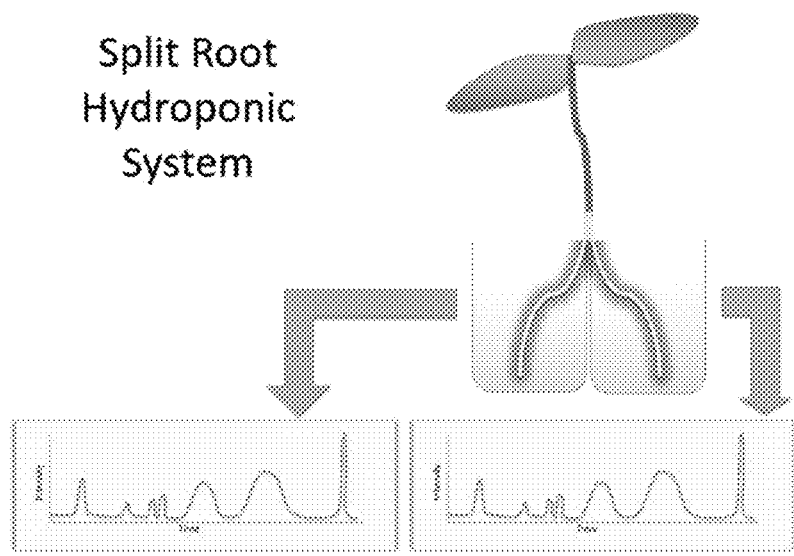
FIG. 2A is a schematic depicting a split root hydroponic system with two root systems growing in separate jars. Root A is on the right, and Root B is on the left. If no inducer is added to any plant compartment (organ), the exudate metabolite profiling of both roots does not change.

Example 5. Rhizodeposition Studies in Metabolomics: Tomato Root Exudates and Soil Bacteria Diversity Rhizodeposition was studied using the M82 cultivar tomato as a model plant using a hydroponic system as described above, in which one plant has two root systems growing in separate jars (FIG. 2A). Untargeted metabolomics were used, combining LC-MS and GC-MS platforms in order to identify the compounds secreted by the plants in a similar manner on both sides of the system.

Figure 2B:
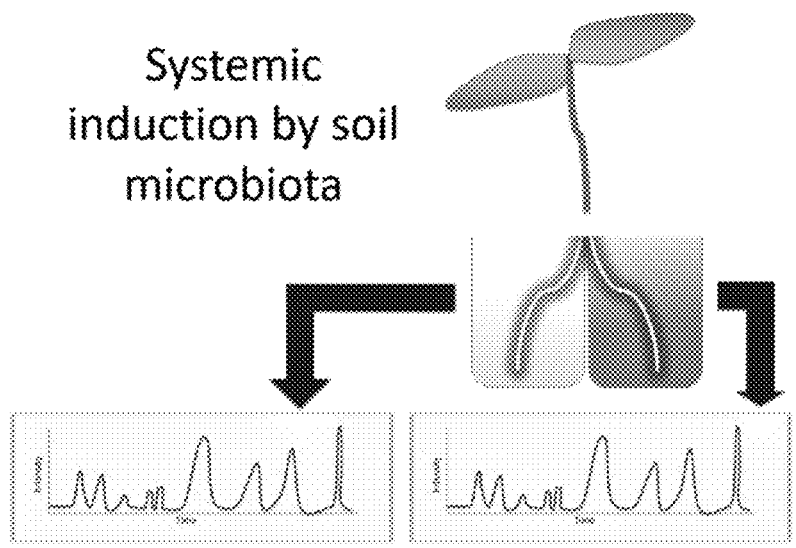
FIG. 2B is a schematic depicting the split root hydroponic system of FIG. 2A after systemic induction by soil microbiota added to Root A (right). After inducer is added, the metabolites that are systemically impacted change as compared to sterile systems.

Autoclaved soil was added to one side of the system (FIG. 2B, right) to enable collection of molecules from root exudates only, exudates that were induced by soil microbiota, but not biodegraded or mixed with molecules of other organisms.

Figure 3:
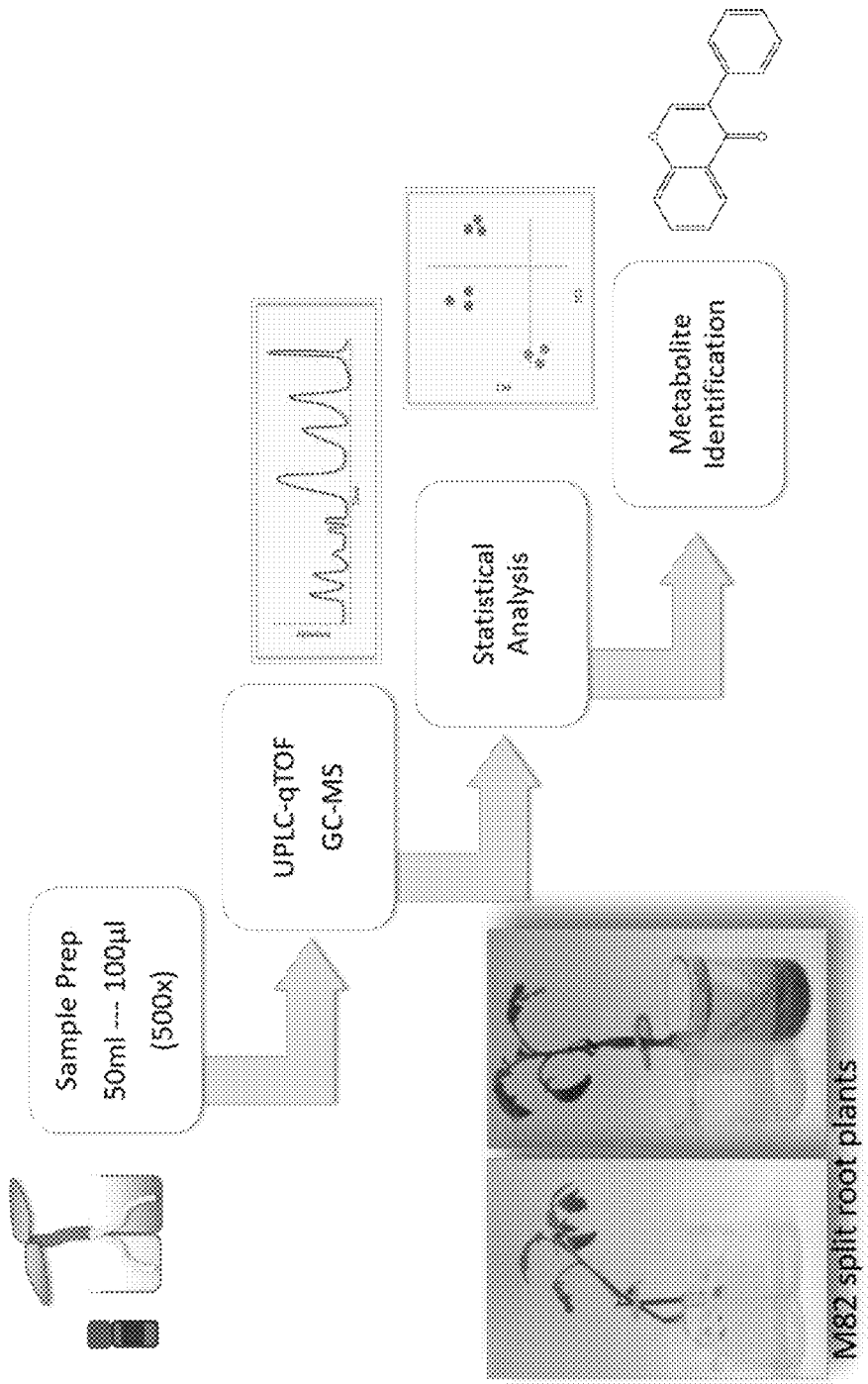
FIG. 3 shows a flow chart for a method of exudate metabolomics workflow utilizing an example of a split root hydroponic method, followed by Sample Prep, detection of compounds via UPLC-qTOF and GC-MS, Statistical Analysis, and Metabolite Identification. Photographs show M82 split root plants, both a control plant (left) and a treated plant (right).
Figure 4:
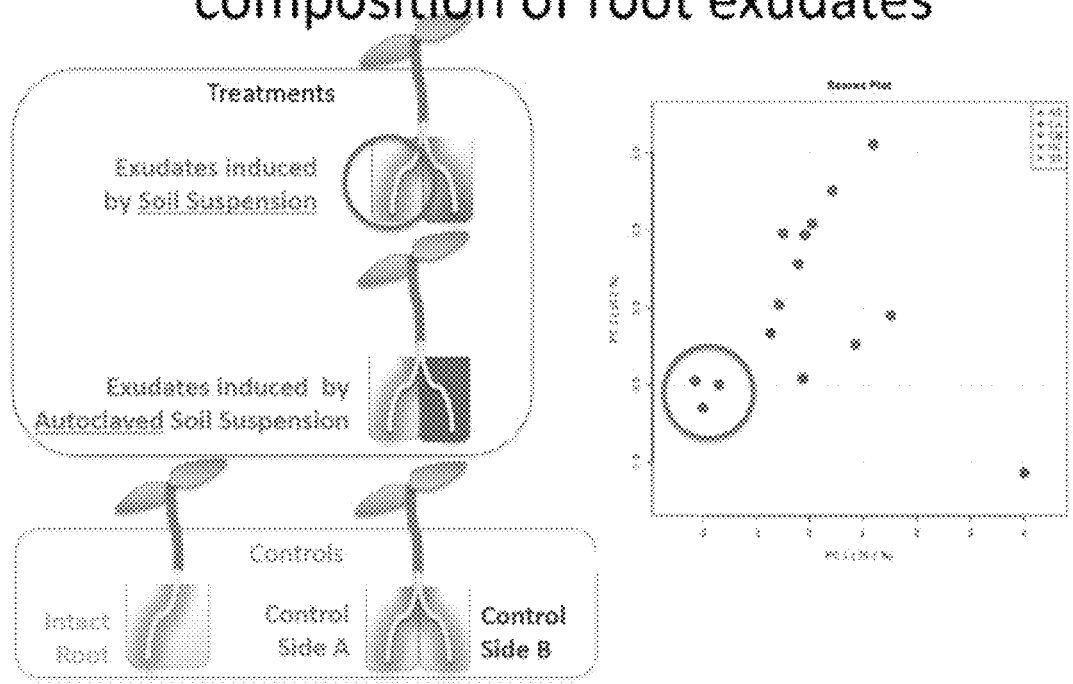
FIG. 4 is a schematic depicting a split root hydroponic method utilizing two types of treatment methods (center left) and two types of controls (bottom left) to study how soil microbiota shape the metabolite composition of root exudates. Controls had either intact roots (aqua) or split roots, the exudates of Root A (green) and Root B (dark blue) being analyzed separately. Treated plants were induced either by soil suspension (pink) or by autoclaved soil suspension (red). Metabolites were analyzed. PCA shows the grouping of metabolite profiling of three treatments (Control without inducer, Autoclaved Soil, Soil), total profiling of metabolites of soil treated plants are indicated in pink.

FIG. 3 depicts a flow chart of an exudate metabolomics workflow method of the present invention. Photographs of two M82 split root tomato plants (control on left, experimental on right) are shown in the lower left corner. The split-root plant was prepared, and soil or autoclaved soil was added. One split root of each experimental plant had its exudates induced by soil suspension or by autoclaved soil suspension (at concentrations of 10-2, 10-4 and 10-6), as compared with split roots treated identically and with intact roots, both as controls (FIG. 3 and FIG. 4). After incubation, sample of 50 ml were removed and reduced to 100 μl (a 500× reduction), followed by both UPLC-qTOF and GC-MS detection methods and statistical analysis. Finally, metabolites were identified, and differences were compared with those of the results of Root A, as well as those of the controls.

Figure 5:
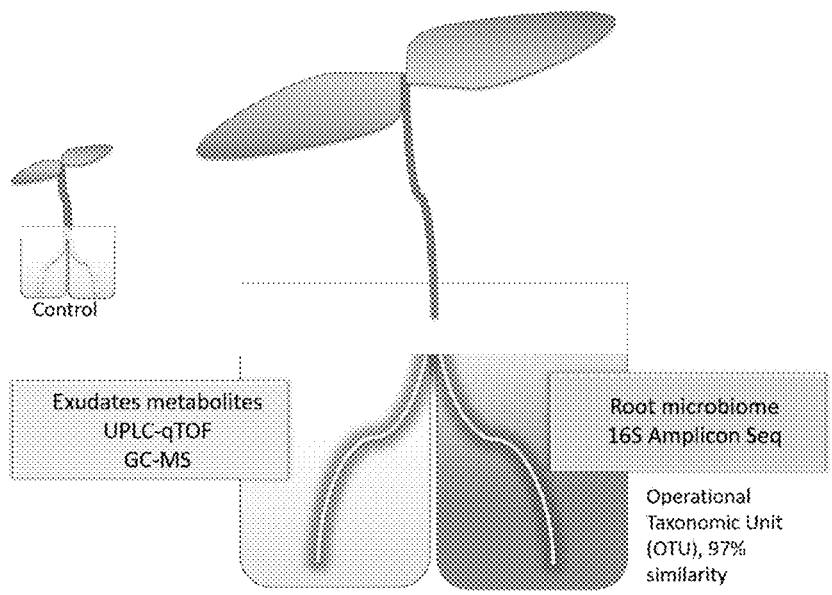
FIG. 5 shows a schematic of a split root hydroponic method. The Control is depicted in the upper left. The treated plant in the center has its exudates/metabolites detected via UPLC-qTOF and GC-MS. The root microbiome is subjected to 16S amplicon sequencing (sequencing of the 16S rRNA gene/rrs gene) as a phylogenetic marker to analyze the bacterial communities according to sequence similarity (SILVA database). Individuals are grouped according to Operational Taxonomic Units (OTU) defined based on a 97% similarity threshold of the total community present.

The 16S rRNA gene (rrs gene) was used as a phylogenetic marker to analyze the bacterial communities according to sequence similarity and using the SILVA database (FIG. 5). Operational Taxonomic Units (OTU) were used as a pragmatic definition to group individuals by similarity, as pragmatic proxies for microbial "species" at different taxonomic levels. Sequences were clustered according to their similarity to one another, and OTUs were defined based on the similarity threshold (usually 97% similarity, in accordance with accepted standards) of the total community present.

Figure 6:
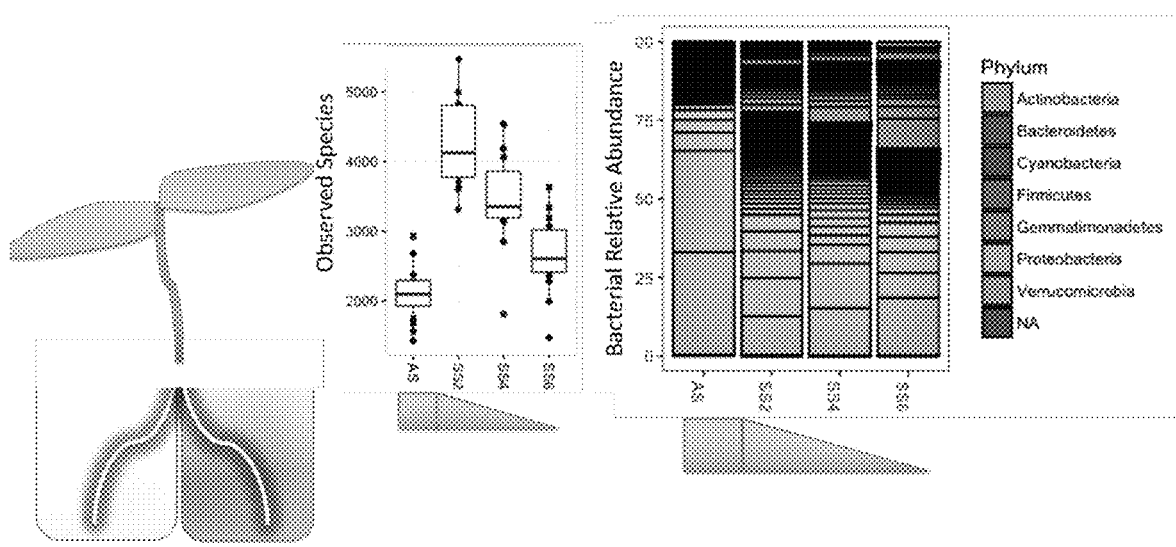
FIG. 6 shows the results of a split root method demonstrating that soil dilution changed the bacterial community structure of roots. The left-hand graph shows the number of observed species (y-axis) in each sample and right-hand bar plot shows the taxonomic distribution in each sample for autoclaved soil (AS), 10-2 soil suspension (SS2), 10-4 soil suspension (SS4), or 10-6 soil suspension (SS6). The bottom plot highlights the decrease in soil microbial diversity. Autoclaved soil was used as the diluent. The right-hand graph shows the relative abundance of bacteria of various phyla (total=100%) for autoclaved soil (AS), 10-2 soil suspension (SS2), 10-4 soil suspension (SS4), or 10-6 soil suspension (SS6). Phyla measured included actinobacteria (red), bacteroidetes (brown), cyanobacteria (dark green), firmicutes (light green), gemmatimonadetes (blue), proteobacteria (purple), verrucomicrobia (pink), and others (NA; black). The bottom plot highlights the decrease in soil concentration.

FIG. 6 shows the results of the study demonstrating the link between the number of observed species in the bacterial community structure as a function of soil dilution (for Root B), with the lowest number of species in the root microbial communities associated with roots induced by autoclaved soil suspension (AS) (FIG. 6, left graph). A dilution-specific decrease was observed in the samples induced by soil suspensions of 10-2 (SS2), 10-4 (SS4), and 10-6 (SS6) (FIG. 6, left graph). The relative abundance of each phylum of bacterial was also analyzed with respect to actinobacteria, bacteroidetes, cyanobacteria, firmicutes, gemmatimonadetes, proteobacteria, verrucomicrobia, and other types (NA) for each of these samples (FIG. 6, right graph). Results demonstrated that soil dilution clearly altered the bacterial community structure on the roots (FIG. 6).

Figure 7:
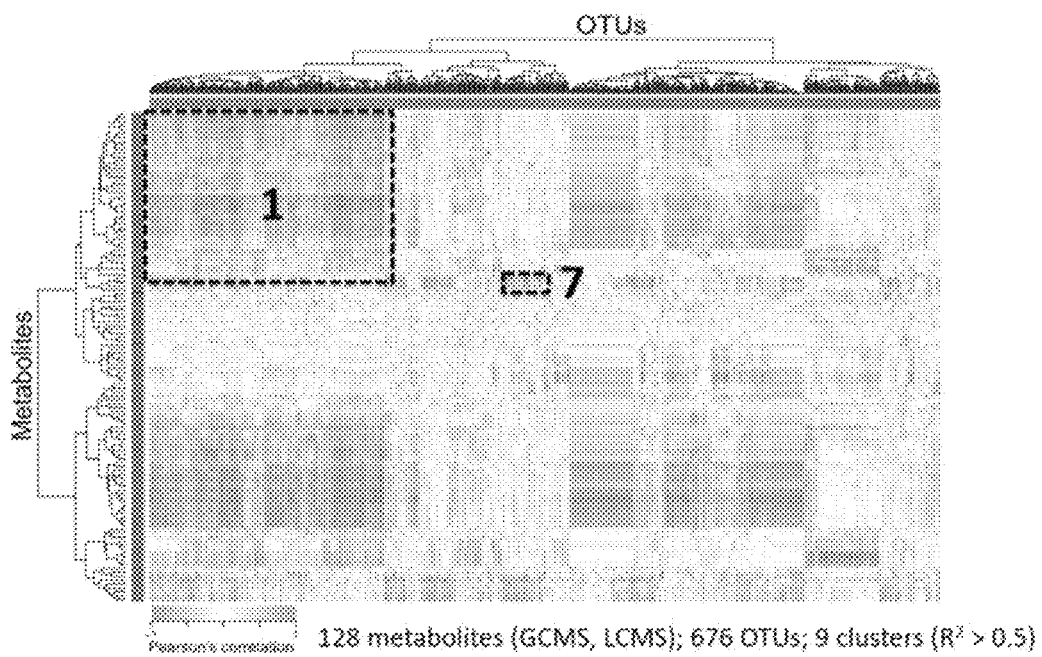
FIG. 7 shows a Pearson's correlation of 128 exuded metabolites (identified by GC-MS and LC-MS) vs. 676 OTUs identifying 9 clusters (R2>0.05) and demonstrating that bacterial abundance correlates with metabolite exudation. Cluster 1 and Cluster 7 are shown (hashed boxes).

With respect to the metabolic profiling of the tomato exudates, GC-MS identified 18 organic acids, 14 carbohydrates, and 10 amino acids, while LC-MS identified 152 metabolites. When metabolite exudation of samples was plotted as a function of bacterial abundance using Pearson's correlation, it was observed that bacterial abundance correlated with metabolite exudation, as shown in FIG. 7. FIG. 7 shows the correlation of 128 metabolites (identified via GC-MS and/or LC-MS) vs. 676 OTUs, which resulted in identification of 9 clusters (Clusters 1 and 7 are marked as shown) (R2>0.5).

Figure 8:
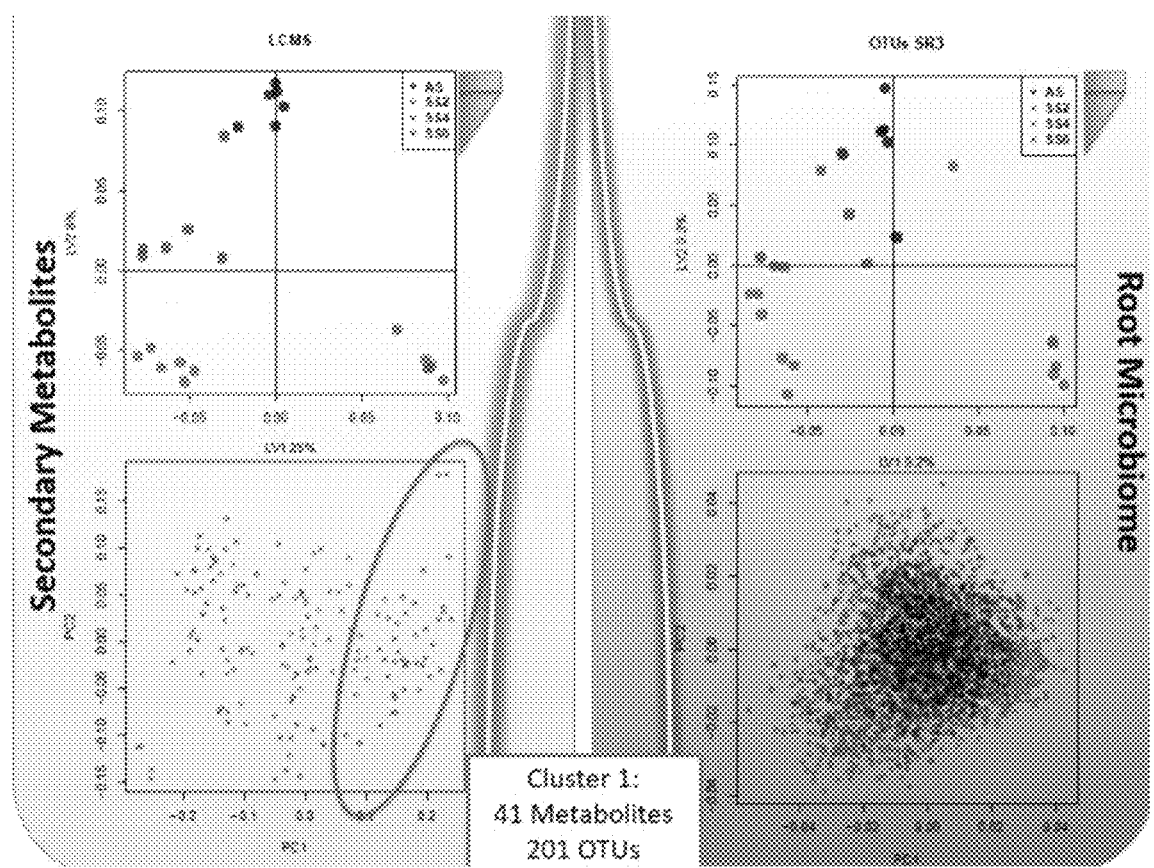
FIG. 8 shows an analysis of Cluster 1 (identified in FIG. 7) analyzing 41 secondary metabolites (left top and bottom) and 201 OTUs (right top and bottom). The ordination plots for each show the clustering of samples according to the metabolome or microbiome data, while the loading plots identify the relationship between the samples and variables (metabolite or OTU). Variables are color according to the cluster codes. The side plots highlight the decrease in soil concentration.

With respect to Cluster 1 (41 metabolites, 201 OTUs), further studies were undertaken (FIG. 8). The ordination plots show the clustering of samples according to the metabolome data (left) or the microbiome data (right). The relationship between the samples and variables (metabolites or OTU) was analyzed in the loading plot. The variables were colored according to their respective cluster codes.

Figure 9A:
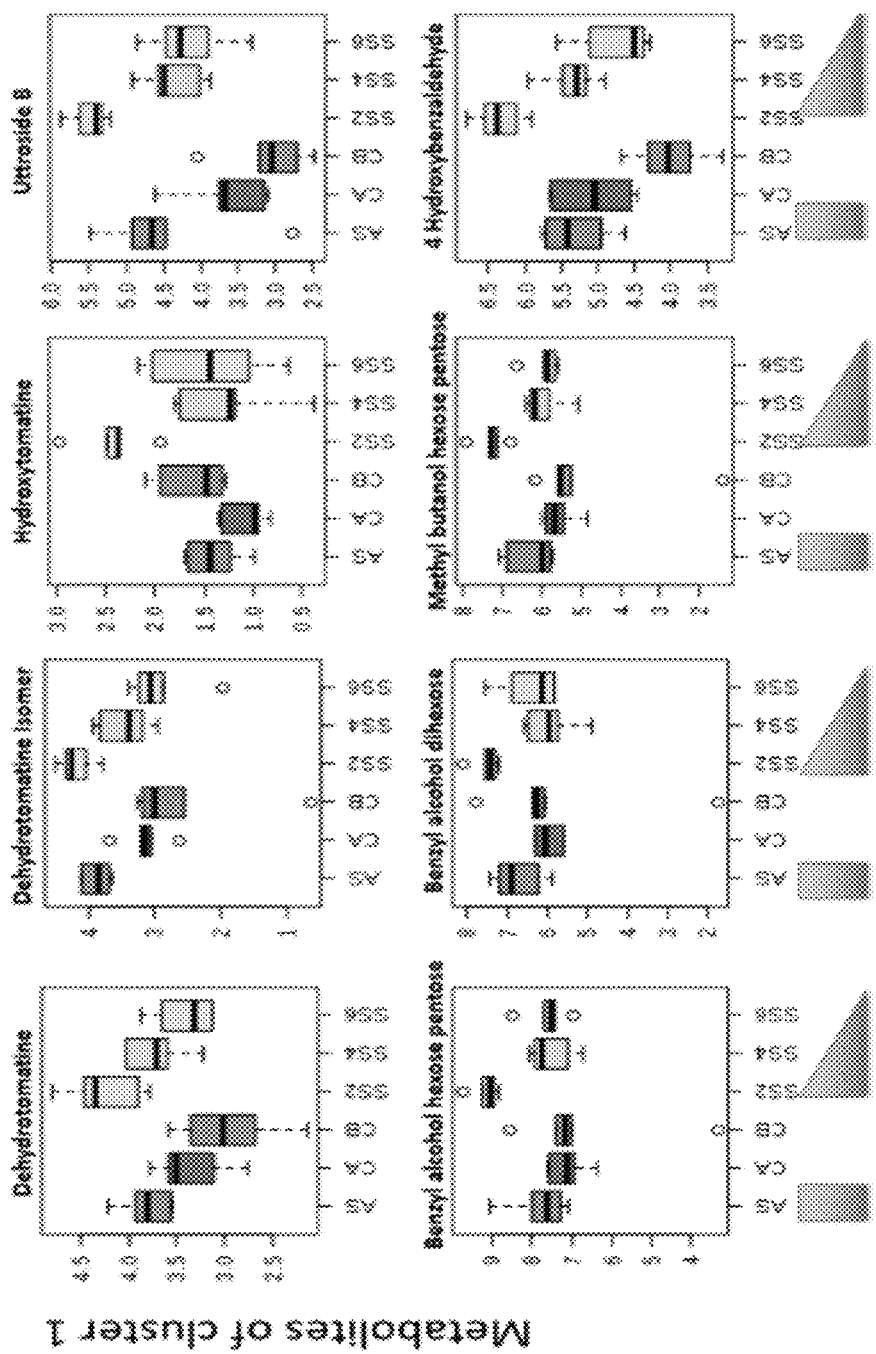
FIG. 9A is a series of box plots showing that the study of the exuded metabolites of Cluster 1 demonstrates that the tomato root exudes more defense molecules in response to increasing bacterial diversity in autoclaved soil (AS), split root control Root A (CA), split root control Root B (CB), 10-2 soil suspension (SS2), 10-4 soil suspension (SS4), or 10-6 soil suspension (SS6). The bottom plots highlight the decrease in soil concentration.

FIG. 9A shows the amounts of various metabolites of Cluster 1 for the samples induced with autoclaved soil (AS) or by soil suspensions of 10-2 (SS2), 10-4 (SS4), and 10-6 (SS6), as well as by CA and by CB. Metabolites studied included dehydrotomatine, dehydrotomatine isomer, hydroxytomatine, uttroside B, benzyl alcohol hexose pentose, benzyl alcohol dihexose, methyl butanol hexose pentose, and 4-hydroxybenzaldehyde (FIG. 9A). Overall, the results demonstrated that the tomato root exudes more defense molecules in environments of high bacterial diversity (FIG. 9A).

Figure 9B:
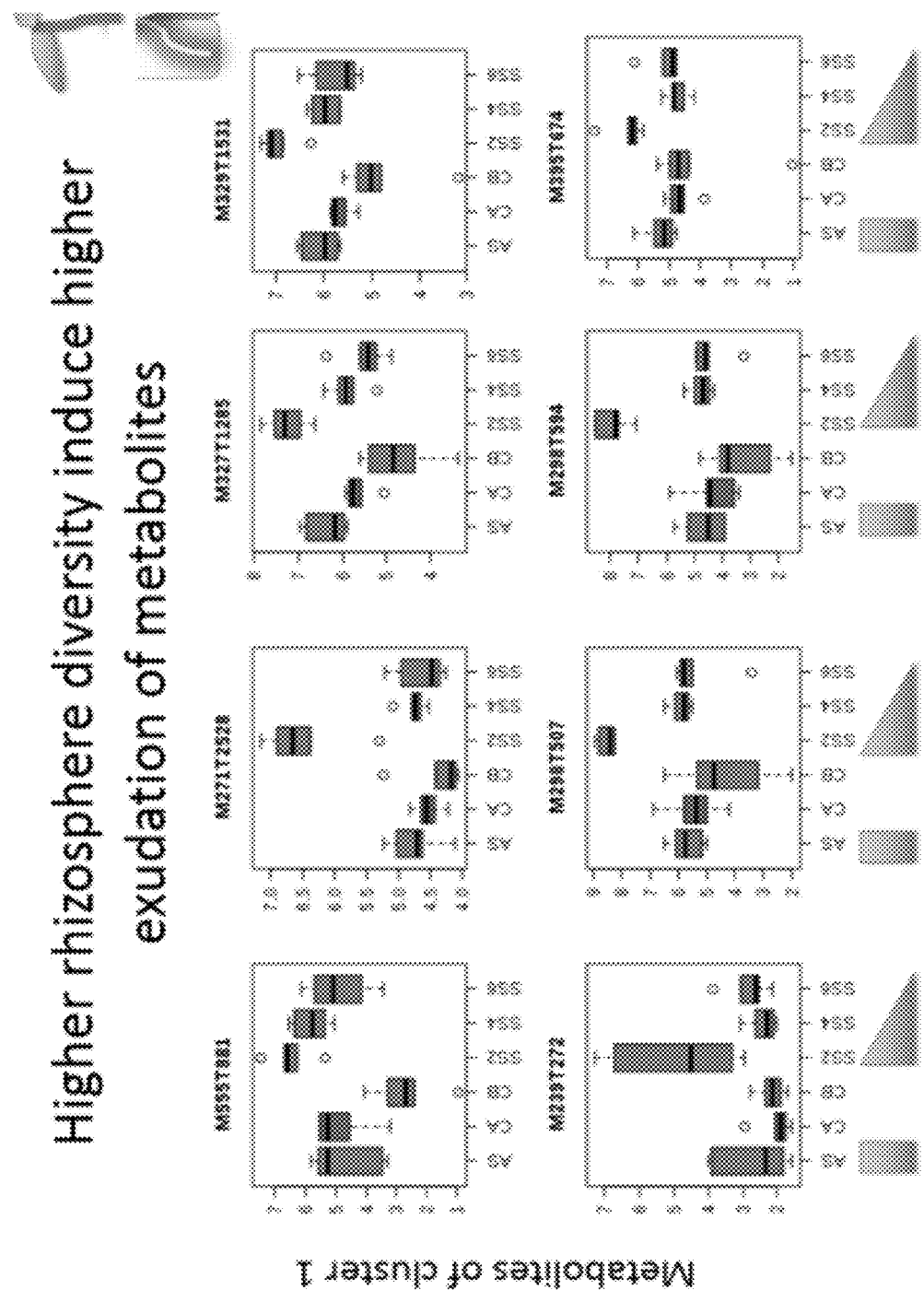
FIG. 9B is a series of box plots showing that the study of the exuded metabolites of Cluster 1 demonstrates that greater rhizosphere diversity induces increased exudation of metabolites in autoclaved soil (AS), split root control Root A (CA), split root control Root B (CB), 10-2 soil suspension (SS2), 10-4 soil suspension (SS4), or 10-6 soil suspension (SS6). The bottom plots highlight the decrease in soil concentration.
Figure 10:
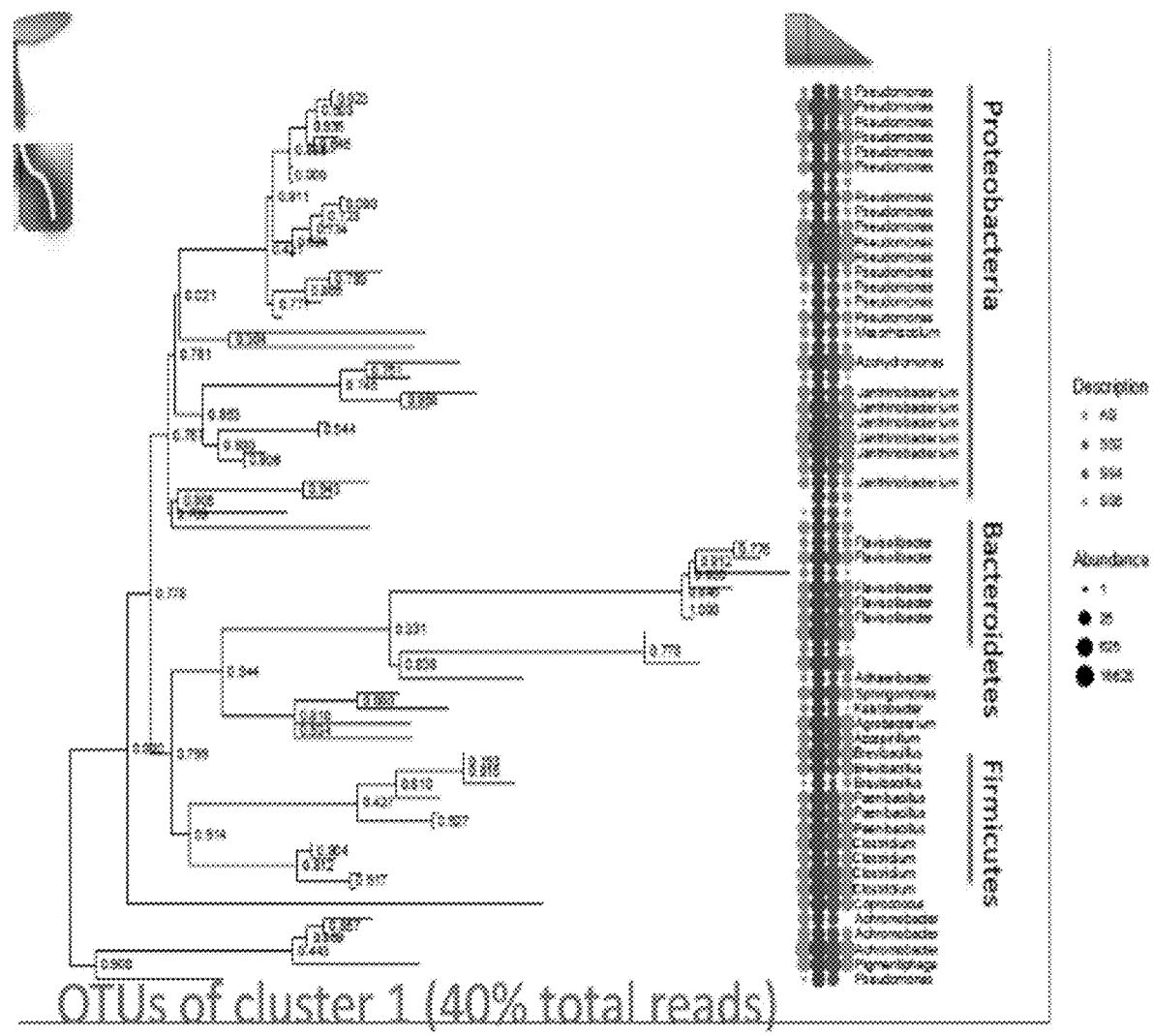
FIG. 10 shows the relative abundance of Proteobacteria, Bacteroidetes, and Firmicutes from Cluster 1 with respect to autoclaved soil (AS) or to soil suspensions of 10-2 (SS2), 10-4 (SS4), and 10-6 (SS6), based on 40% total reads of OTUs of Cluster 1.

FIG. 9B shows the amounts of various metabolites of Cluster 1 for the samples induced with autoclaved soil (AS) or by soil suspensions of 10-2 (SS2), 10-4 (SS4), and 10-6 (SS6), as well as by CA and by CB. Metabolites studied included M555T881, M271T2528, M327T1285, M239T1531, M239T272, M298T507, M298T594, and M395T674 (FIG. 9B). Overall, the results demonstrated that a greater rhizosphere diversity induces a greater exudation of metabolites (FIG. 6B). FIG. 10 shows the relative abundance of proteobacteria, bacteroidetes, and firmicutes from Cluster 1 with respect to autoclaved soil (AS) or to soil suspensions of 10-2 (SS2), 10-4 (SS4), and 10-6 (SS6), based on 40% total reads of OTUs of Cluster 1.

Defense molecules were highly secreted in high bacterial diversity samples, likely due to bacteria present in Cluster 1 (*Pseudomonas*, Janthinobacterium, Flvisolibacter, *Paenibacillus*).

Figure 11:
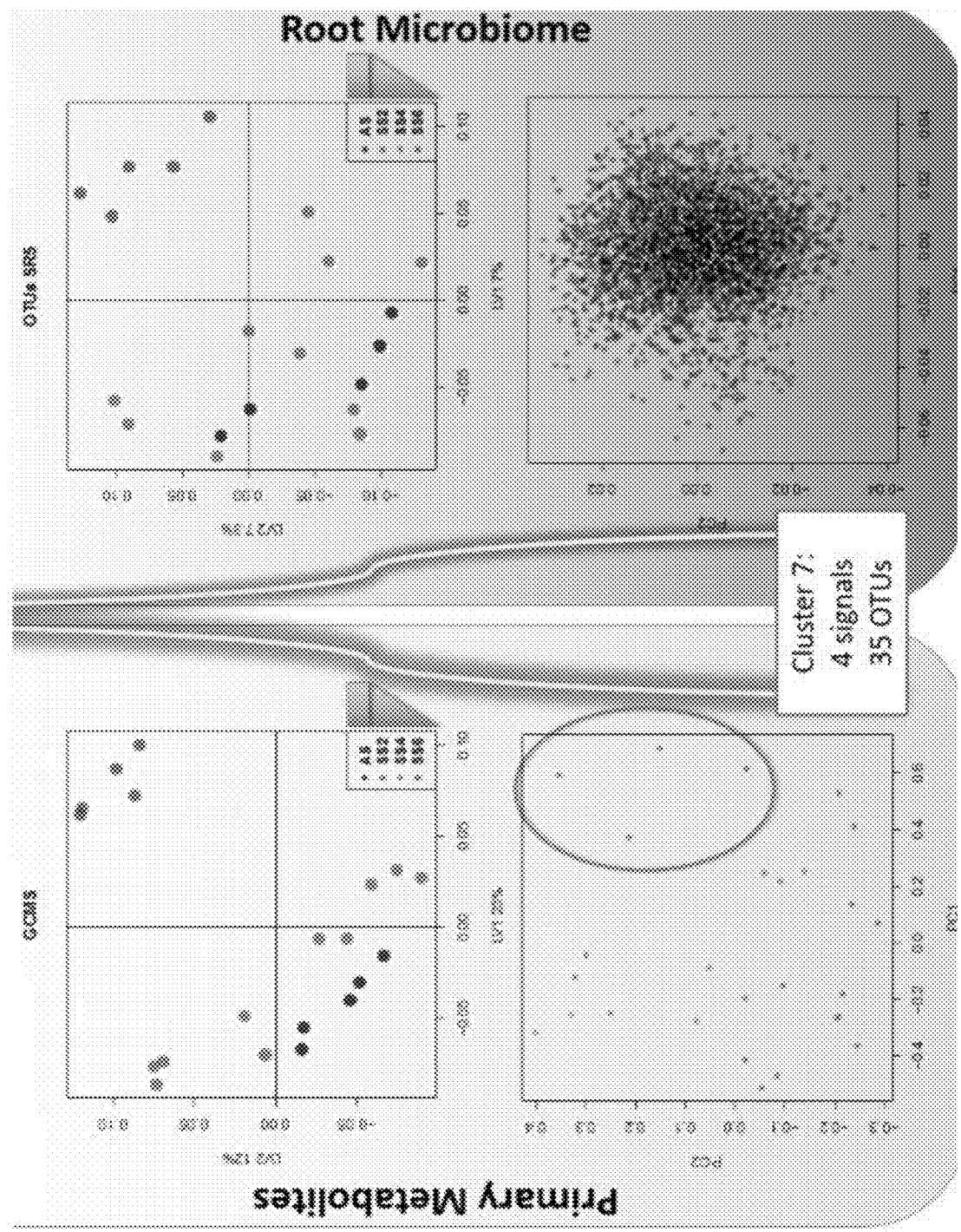
FIG. 11 shows an analysis of Cluster 7 (identified in FIG. 7) analyzing 4 primary metabolites (left top and bottom) and 35 OTUs (right top and bottom). The ordination plots for each show the clustering of samples according to the metabolome or microbiome data, while the loading plots identify the relationship between the samples and variables (metabolite or OTU). Variables are color according to the cluster codes. The side plots highlight the decrease in soil concentration.

A similar analysis was performed on Cluster 7 (FIG. 7). With respect to Cluster 7 (4 signals, 35 OTUs), further studies were undertaken (FIG. 11). The ordination plots show the clustering of samples according to the metabolome data (left) or the microbiome data (right). The relationship between the samples and variables (metabolites or OTU) was analyzed in the loading plot. The variables were colored according to their respective cluster codes.

Figure 12:
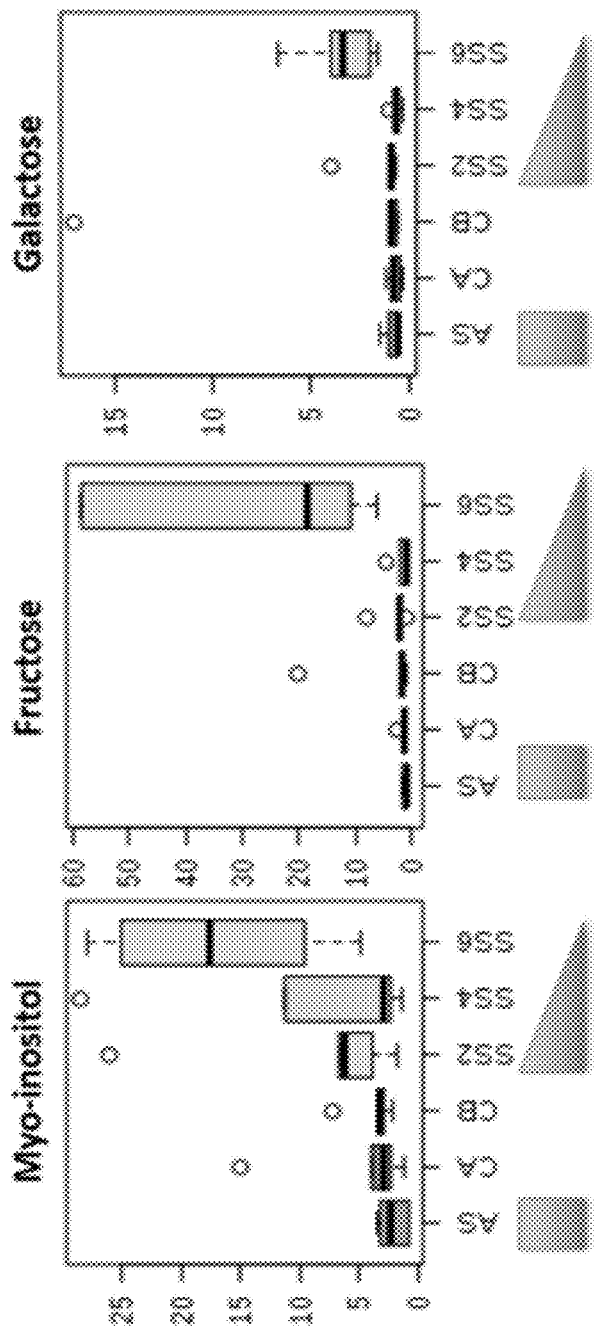
FIG. 12 is a series of box plots showing that the study of the exuded sugar metabolites of Cluster 7 demonstrates that sugars are exuded at higher levels in environments of low bacterial diversity in autoclaved soil (AS), split root control Root A (CA), split root control Root B (CB), 10-2 soil suspension (SS2), 10-4 soil suspension (SS4), or 10-6 soil suspension (SS6). The bottom plots highlight the decrease in soil concentration.
Figure 13:
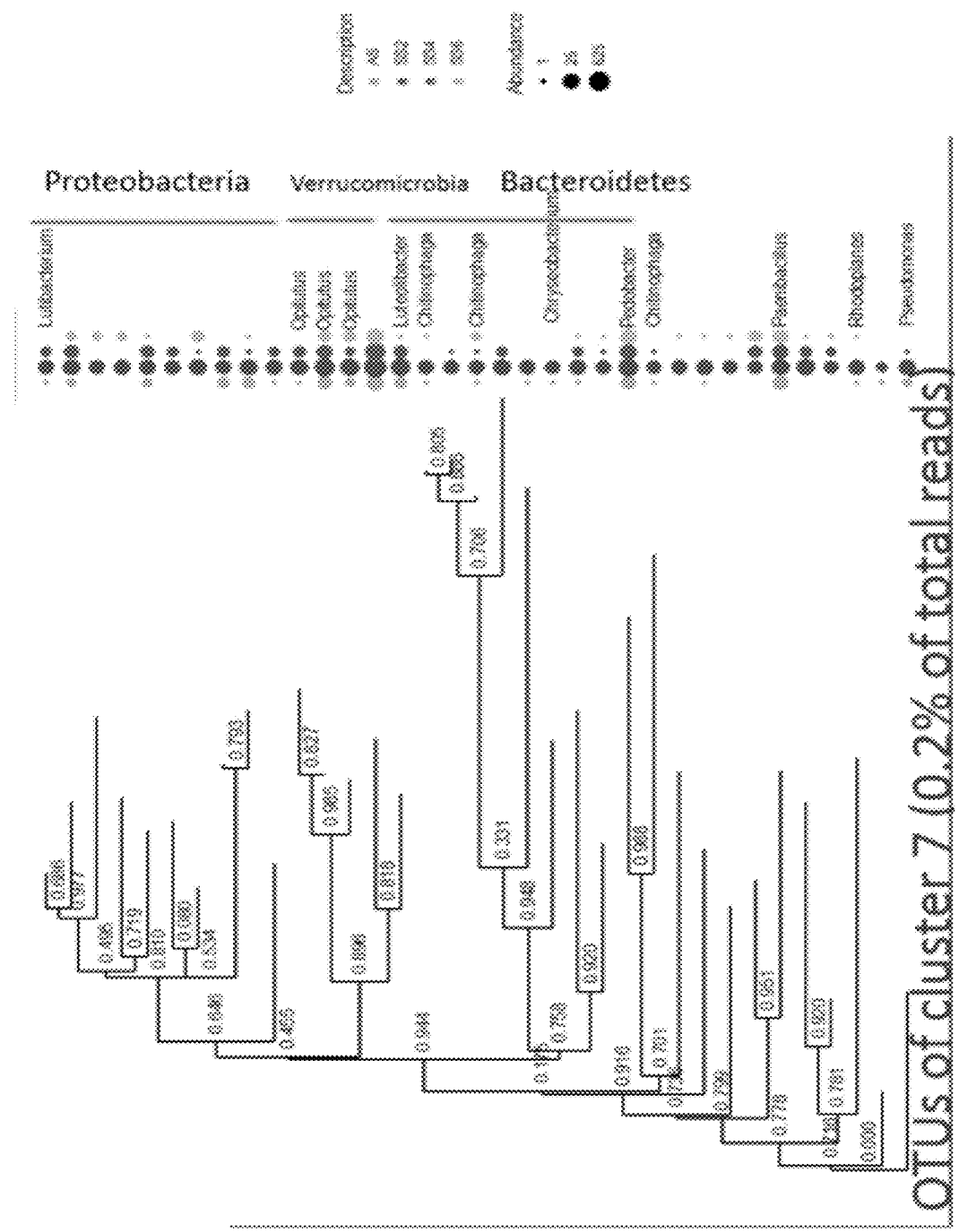
FIG. 13 shows the relative abundance of Proteobacteria, Bacteroidetes, and Firmicutes from Cluster 7 with respect to autoclaved soil (AS) or to soil suspensions of 10-2 (SS2), 10-4 (SS4), and 10-6 (SS6), based on 0.2% total reads of OTU of Cluster 7.

FIG. 12 shows the amounts of various metabolite sugars of Cluster 7 for the samples induced with autoclaved soil (AS) or by soil suspensions of 10-2 (SS2), 10-4 (SS4), and 10-6 (SS6), as well as by CA and by CB. Metabolite sugars studied included myo-inositol, fructose, and galactose (FIG. 12). Overall, the results demonstrated that the tomato root exudes sugars more in environments of low bacterial diversity (FIG. 12). FIG. 13 shows the relative abundance of proteobacteria, bacteroidetes, and firmicutes from Cluster 7 with respect to autoclaved soil (AS) or to soil suspensions of 10-2 (SS2), 10-4 (SS4), and 10-6 (SS6), based on 0.2% total reads of OTU of Cluster 7.

Sugars were highly secreted in low diversity samples, possibly induced by low-abundance fermentative bacteria (Opitutus, Chitinophaga).

Example 6. Production of Tomato Alkaloids from Tomato Plants

Tomatoes were studied using split root technology using the methods of Example 2. After lateral roots emerged, roots were aseptically placed separately in two 20 ml glass containers containing 0.5× Hoagland nutrient solution. Root A was stimulated with 3 different soil microbial communities (diverging on structure and abundance, (FIG. 17). Plants were incubated at 24° C. with a photoperiod of 16 h.

Figure 14:
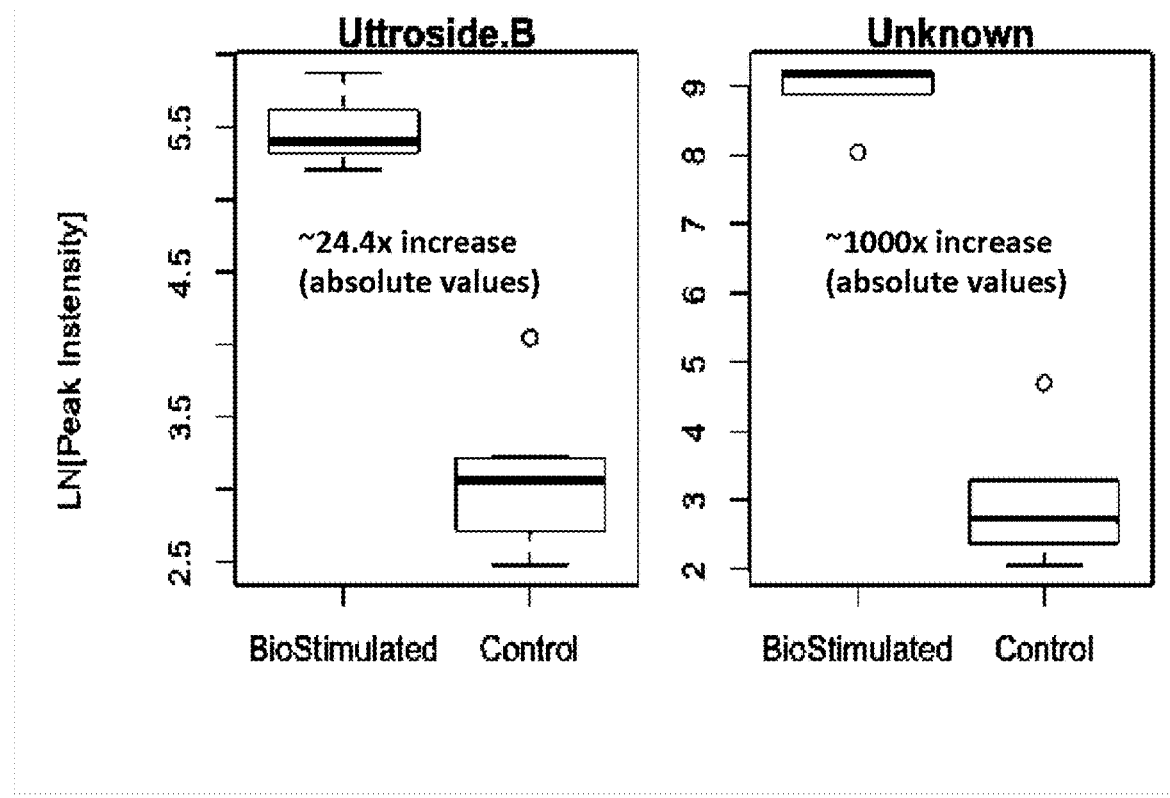
FIG. 14 shows plots demonstrating the increase in secretion of specialized metabolites after tomato plants were bio-stimulated using split root methodology. Shown are increases in uttroside B (left) and a novel metabolite (right).

A week after microbial pool stimulation (FIG. 17), the plant medium containing exudates from Root B was collected, filtered and extracted for LC-MS non-targeted analysis. Tomato bio-stimulated exudates from Root B displayed systemically higher exudation of various metabolites according to the microbial community added to Root A. Using split root technology, approximately 100 metabolites were induced by one of the microbial pools leading to a systemic induction of metabolite secretion in Root B. FIG. 14 shows two examples; uttroside B (a promising saponin with chemotherapeutic activity against hepatocellular carcinoma) was released in the plant medium of Root B 24 times more than in control non-stimulated plants (FIG. 14, left), and an unidentified metabolite was 1000 times higher in Root B from the bio-stimulated tomato plants as compared to control plants (FIG. 14, right). Bio-stimulation used for this technology is also a method for drug discovery.

Example 7. Production of Tomato Alkaloids as Exudates

Larger scale production of tomato alkaloids is performed. Tomato plants are grown using the split-root methodology as described in Examples 2 and 5.

Root A is stimulated according to Example 5. The soil medium from each Root B is collected, and uttroside B is isolated and purified.

Example 8. Production of Taxol from *Taxus baccata*

For *Taxus baccata* plants, the methods of Example 1 were used to obtain split roots. Both root systems were places in two 50 ml falcon tubes containing 0.1× MS plant medium. The root A of the tree seedlings was stimulated with the fungus *Trichoderma hamatum* fungus and with methyl jasmonate, while growing in hydroponics using plant nutrient medium. Plants were incubated at 24° C. with a photoperiod of 16 h. A week after stimulation, the plant medium containing exudates from Root A and B were collected, filtered and extracted for LC-MS analysis. Taxanes were highly induced and secreted locally by stimulated plants in roots. FIGS. 15A and 15B depict the MRM-LC-MS/MS of *Taxus* exudates. Taxol (FIG. 15A) and 10-DAB (FIG. 15B) were analyzed via total ion current chromatograms. Taxol was approximately 300× more exuded from Root A in stimulated plants as compared to plants before stimulation or to Root B (FIG. 15A). In addition, the biosynthetic intermediate of taxol, 10-deacetyllbaccatin III (10-DAB) was also locally bio-stimulated and secreted 78 times more than the non-stimulated plants (FIG. 15B). The quantification of three taxanes (10-DAB, Baccatin III and Taxol) was performed using an external standard curve of these three metabolites (FIG. 15C); 10-DAB and Baccatin III were highly induced after first bio-stimulation with fungus and methyl jasmonate, approximately 15 μg/L in exudates from side A, while Taxol concentrations in exudates reached 3 μg/L in the first bio-stimulation and 2 μg/L after second bio-stimulation. Time of bio-stimulation is an important factor for secondary metabolites production optimization.

Example 9. Production of Taxanes as Exudates

Larger scale production of taxanes is performed. *Taxus* plants are grown using the split-root methodology as described in Examples 1 and 8. Root A is stimulated with *Trichoderma hamatum* fungus or with methyl jasmonate according to Example 8. The soil medium from each Root A is collected, and the exudates Taxol, 10-DAB, and/or Baccatin III are harvested.

Example 10. Production of Vinca Alkaloids from *Catharanthus roseus*

*Catharanthus roseus* were grown, and split roots were obtained using the methods of Example 2. After lateral roots emerged, roots were aseptically placed separately in two 20 ml glass containers containing 0.5× Hoagland nutrient solution. Similar to Example 8, Root A of seedlings was stimulated with methyl-jasmonate, while growing in hydroponics using plant nutrient medium. Plants were incubated at 24° C. with a photoperiod of 16 h. A week after stimulation, the plant medium containing exudates from Root A and B were collected, filtered and extracted for LC-MS analysis. FIG. 16A depicts the MRM-LC-MS/MS analysis of *C. roseus* exudates. Vinca alkaloids present in the exudates of Root B after methyl jasmonate stimulation (FIG. 16A, top) and control plants (FIG. 16A, bottom) were analyzed via total ion current chromatograms. The quantification of three vinca alkaloids (19S-Vindolinine_RT_3.93, Vindolinine_RT_4.96, and Catarantine_11.77) was performed using an external standard curve of these three metabolites (FIG. 16B). Methyl jasmonate applied to Root A of *C. roseus* induced systemically higher exudation of terpenoid indole alkaloids in Root B using split root technology, e.g., up to 32× more Vindolinine was found in Root B of plants treated with methyl jasmonate.

Example 11. Production of Alkaloids as Exudates

Larger scale production of vinca alkaloids and/or terpenoid indole alkaloids is performed. *C. roseus* plants are grown using the split-root methodology as described in Examples 2 and 10. Root A is stimulated with methyl jasmonate according to Example 10. The soil medium from each Root B is collected, and the exudate vinca alkaloids (e.g., 19S-vindolinine_RT_3.93, vindolinine_RT_4.96, and/or catarantine_11.77) and/or terpenoid indole alkaloids are harvested.

Example 12. Production of Exudates from *Cannabis sativa*

*Cannabis sativa* are grown, and split roots are obtained using the methods of Example 1 or Example 2. Split roots or lateral roots are aseptically placed separately in two 20 ml glass containers containing nutrient solution. Root A of seedlings is stimulated, such as with methyl jasmonate or another stimulant, while growing in hydroponics or aeroponics using plant nutrient medium. Plants are incubated, e.g., at 24° C. with a photoperiod of 16 h. A week after stimulation, the plant medium containing exudates from Root A or Root B is collected, filtered and extracted for analysis.

Example 13. Production of Cannabinoids, Terpenoids, Metabolites, Intermediates, or Other Molecules from *Cannabis sativa*

*C. sativa* is grown and treated according to Example 12. The plant medium containing exudates is collected, filtered, and extracted. Further isolation of cannabinoids or of other metabolites, intermediates, or other molecules of interest (e.g., pharmaceutical compounds) from the collected exudates is performed.

Example 14. Production of Exudates from *Pappaver somniforum*

*Pappaver somniforum* (opium poppies) are grown, and split roots are obtained using the methods of Example 1 or Example 2. Split roots or lateral roots are aseptically placed separately in two 20 ml glass containers containing nutrient solution. Root A of seedlings is stimulated, such as with methyl jasmonate or another stimulant, while growing in hydroponics or aeroponics using plant nutrient medium. Plants are incubated, e.g., at 24° C. with a photoperiod of 16 h. A week after stimulation, the plant medium containing exudates from Root A or Root B is collected, filtered and extracted for analysis.

Example 15. Production of Alkaloids, Metabolites, Intermediates, or Other Molecules from *Pappaver somniforum*

*P. somniforum* is grown and treated according to Example 14. The plant medium containing exudates is collected, filtered, and extracted. Further isolation of alkaloids, such as opium, thebaine, or oripavine, or of other metabolites, intermediates, or other molecules of interest (e.g., pharmaceutical compounds) from the collected exudates is performed.

Example 16. Coupling Metabolic Engineering to Engineered Secretion of Molecules from the Plant Roots in Model and Non-Model Plants A more advanced system for the harvest of high value products from plant root exudation (i.e., extending collection of plant root exudation beyond natural secretion from the plant) is through engineering plants for synthesis and secretion from roots. Examples include, but are not limited to, plants that do not produce such molecules or exude them naturally.

In this approach, a plant, such as a tobacco or tomato plant, is engineered for the production of a particular molecule. This is accomplished, for example, by using tools of genetic engineering, such as by overexpression using constitutive or cell-type specific or induced promoters, or genome editing by introducing an activation or repression element. For engineering, the biosynthesis of a particular molecule or molecules silencing through RNA interference or genome editing as above can be used. In some examples, a combination of overexpression and silencing will be required to engineer a metabolic pathway, and the number of genes introduced (isolated from any living creature) is not limited.

For example, the entire cholesterol pathway containing 12 genes has been engineered in plants as an example of a gene 'stitching' approach for engineering of target products/molecules (Sonawane, P. D., Pollier, J., Panda, S., et al. (2016) Plant cholesterol biosynthetic pathway overlaps with phytosterol metabolism. Available at: https://www.nature.com/articles/nplants2016205.pdf [Accessed Mar. 7, 2018]).

The approach for harvesting root exudates using the system of the present invention couples the engineering of a molecule with the required transporter protein (e.g., from any class ATP-Binding Cassette-type, MATE-type, or NRT-type). The coupled transporter protein has either high specificity to the molecule or is able to transport a range of molecules either one with similar or dissimilar structure. The engineering of the transporter protein for expression in the root outer layers, either in the root cap cells or the epidermis, is highly preferable as well as in the lateral roots. The transgenic plant may produce a coupled transporter protein specific for transporting the molecule of interest, e.g., even a single enzyme overexpressed or downregulated in different molecular ways such that the transporter protein is couple with an engineered pathway in order for the specific transporter protein to transport the molecule of interest out to the environment (e.g., soil, liquid medium, air, etc.).

The transport activity transports the target molecule, either constitutive or induced, from the inner root cells to the outside medium in which the plant grows, i.e. in a soil, hydroponics or aeroponics milieu. The engineered plants are grown for harvest continuously in or out doors, and the system for harvesting exudates is all underground (even for trees) as detailed below. (Alternatively, the system for harvesting exudates is above ground, as described, e.g., in Example 18, below.)

As in natural environments and also here, plant exudation of molecules is triggered by, e.g., hormones, specific microbial strains, synthetic microbial communities, microorganism parts, and other elicitors. Microbial strains with selected functions are pooled and collectively form a simplified synthetic community, i.e. few dozen species with selected abundances (cell concentration). This synthetic microbial community is used as a bio-tool to modulate host metabolism to induce the candidate metabolites and increase exudation. For example, microbial communities are controlled by inoculating plant growing in aseptic conditions with selected microbial strains or natural communities that can be manipulated by pH or other abiotic parameters, addition of amendments (e.g. antibiotics). In addition, engineered microbial strains with specific functions can also be part of the synthetic community in order to optimize host metabolism for exudation.

Example 17. A System of Stimulation Using Volatile Compounds

Stimulaton of the plant is performed using volatile or airborne molecules or a mixture of volatile or airborne molecules, which is introduced to the vial (e.g., into which a split root has been placed) or which is applied on the upper part (e.g., the aerial portion) of the plant.

Example 18. A System for Harvest of Exudates/Metabolites Secreted from Plant Roots Harvest of exudates/metabolites is done through a system in which a set of pipes collects the exudate and passes it through specific columns, each of which concentrates the desired molecule on it. In this way, the target molecule is harvested continuously and concentrated immediately on the column. Every day or two the column is replaced by a new one and the metabolites collected are eluted and available for downstream steps (used either as is or undergoing further purification). This pipe system can be in a growth chamber, greenhouse or underground outside.

Using this system, exudates can be collected also, without passing them through a column.

Example 19. An Underground System for Harvest of Exudates/Metabolites Secreted from Plant Roots Harvest of exudates/metabolites is done through an underground system in which a set of underground pipe system collects the exudate and passes it through specific columns, each of which concentrates the desired molecule on it. In this way, the target molecule is harvested continuously and concentrated immediately on the column. Every day or two the column is replaced by a new one and the metabolites collected are eluted and available for downstream steps (used either as is or undergoing further purification). This underground pipe system can be in a growth chamber, greenhouse or underground outside.

Using this system, exudates can be collected also, without passing them through a column.

Example 20. Plants as Biostimulants

Plants themselves, or a series of plants, can be used as biostimulants in the present invention. A portion of a plant may also be used.

A plant of the same or of a different species can serve as a biostimulant. Alternatively, a series of split-root plants (either the same or different species) can be used in pair or in a group or series.

Example 21. Recycling of Bio-Stimulated Plants and Portions Thereof

Bio-stimulated plants used to withdraw exudates can be recycled if certain metabolites are accumulated inside the plants, i.e., in roots or aerial parts (shoots, leaves, trunk). For example, trees, bushes, cacti, and certain other plants are organisms that live for long periods of time, and exudation collection is the primary goal. Nevertheless, when the expected life cycle is about to end, bio-stimulated parts of a longer-lived plant are used directly for 'harvesting' of specialized metabolites and high value molecules, such as by isolated metabolites directly from the bio-stimulated part of the plant (e.g., the root moiety from which the exudate of interest is secreted).

Alternatively, in the case of shoot or root regeneration and re-branching of a tree, bush, cactus, or other longer-lived plant, a bio-stimulated part of the plant is also used for direct 'harvesting' of specialized metabolites and high value molecules.

In the case of plants that live for a short-term, methods of recycling bio-stimulated plant parts that also accumulate the candidate metabolite are used.

Moreover, some specialized metabolites can be accumulated after bio-stimulation inside the plants only, and the metabolite of interest is harvested directly from the body of the plant.

Variations, modifications, and other implementations of what is described herein will occur to those of ordinary skill in the art without departing from the spirit and scope of the invention.

The foregoing examples demonstrate experiments performed or contemplated by the present inventors in making and carrying out the invention. It is believed that these examples include a disclosure of techniques which serve both to apprise the art of the practice of the invention and to demonstrate its usefulness. Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

All of the references identified hereinabove and hereinbelow, are hereby expressly incorporated herein by reference to the extent that they describe, set forth, provide a basis for or enable compositions and/or methods which may be important to the practice of one or more embodiments of the present inventions.

The invention claimed is:

1. A method for obtaining an exudate from a *Cannabis sativa* root, the method comprising:
   a) providing *Cannabis sativa*;
   b) splitting a root of the *Cannabis sativa* into at least two root moieties;
   c) placing each root moiety of the *Cannabis sativa* into a separate container or compartment;
   d) stimulating a first root moiety of the *Cannabis sativa* or an aerial portion of the *Cannabis sativa* with methyl jasmonate to induce exudation or secretion of an exudate by the second root moiety of the *Cannabis sativa* into the container or compartment of the second root moiety; and
   e) harvesting the exudate from the container or compartment wherein said exudate comprises a metabolite of interest, wherein said metabolite of interest comprises a cannabinoid, a terpenoid, or a combination thereof.

2. The method of claim 1, wherein said obtaining said exudate is obtaining a composition comprising at least 30% w/w exudate.

3. The method of claim 1, wherein said obtaining an exudate is obtaining a composition comprising at least 30% w/w exudate without any enrichment or a purification step.

* * * * *